(12) United States Patent
Tojo et al.

(10) Patent No.: US 8,529,509 B2
(45) Date of Patent: Sep. 10, 2013

(54) SYRINGE DRIVE DEVICE AND MEDICATION DISPENSING APPARATUS

(75) Inventors: Tsuyoshi Tojo, Osaka (JP); Soichiro Fujioka, Osaka (JP); Tohru Nakamura, Osaka (JP)

(73) Assignee: Panasonic Corporation, Osaka (JP)

( * ) Notice: Subject to any disclaimer, the term of this patent is extended or adjusted under 35 U.S.C. 154(b) by 60 days.

(21) Appl. No.: 13/322,650

(22) PCT Filed: Jul. 22, 2010

(86) PCT No.: PCT/JP2010/004697
§ 371 (c)(1),
(2), (4) Date: Nov. 28, 2011

(87) PCT Pub. No.: WO2011/010466
PCT Pub. Date: Jan. 27, 2011

(65) Prior Publication Data
US 2012/0071828 A1 Mar. 22, 2012

(30) Foreign Application Priority Data
Jul. 23, 2009 (JP) .................................. 2009-171701

(51) Int. Cl.
*A61M 37/00* (2006.01)

(52) U.S. Cl.
USPC .......................................... 604/131; 604/218

(58) Field of Classification Search
USPC ............. 604/65–67, 131, 151, 154–155, 187, 604/218, 224, 228, 152
See application file for complete search history.

(56) References Cited

U.S. PATENT DOCUMENTS
2007/0235083 A1 * 10/2007 Dlugos ........................ 137/223

FOREIGN PATENT DOCUMENTS
JP  1-244759  9/1989
JP  5-42213   2/1993

OTHER PUBLICATIONS

International Search Report issued Aug. 24, 2010 in International (PCT) Application No. PCT/JP2010/004697.
English translation of International Preliminary Report on Patentability issued Feb. 16, 2012 in International (PCT) Application No. PCT/JP2010/004697.

* cited by examiner

*Primary Examiner* — Theodore Stigell
(74) *Attorney, Agent, or Firm* — Wenderoth, Lind & Ponack, L.L.P.

(57) ABSTRACT

A syringe drive device 1 includes: a syringe holding section 3; a piston manipulating section 4; and a display section 6. An outer tube 202 of a syringe 201 is detachably held by the syringe holding section 3. A piston 203 of the syringe 201 is detachably engaged with the piston manipulating section 4. The piston manipulating section 4 moves in a direction in response to an operation of operation buttons 8A and 8B, and the piston 203 is thereby moved in a direction where the piston is pushed into or pulled out from the outer tube 202. An internal pressure of a medicinal solution container punctured with an injection needle 204 attached to the outer tube 202 of the syringe 201 is measured and displayed on the display section 6.

14 Claims, 15 Drawing Sheets

SYRINGE DRIVE DEVICE AND MEDICATION DISPENSING APPARATUS

TECHNICAL FIELD

The present invention relates to a syringe drive device configured to move a piston (plunger) of a syringe, which is used in a medication dispensing operation, such as a mixing operation to prepare an injection solution or an intravenous solution, relative to an outer tube (barrel). The present invention further relates to a medication dispensing apparatus to which such a syringe drive apparatus is applied.

BACKGROUND ART

In a conventional mixing operation to prepare an injection solution or an intravenous solution, aspirating a medicinal solution in a vial (medicinal solution container) into a syringe or injecting a medicinal solution in a syringe into a vial is manually carried out by an operator. In these processes, an injection needle attached to an edge of the syringe is punctured into a rubber cap of the vial so that the inside of the syringe and the vial form an enclosed space.

When the medicinal solution contained in the vial is aspirated into the syringe, a piston provided in the syringe is moved in a direction where the piston is pulled out from an outer tube. Internal pressure of the vial decreases with increasing amount of medicinal solution that was aspirated into the syringe, increasing a force required to drive the piston. When the injection needle is pulled out from the vial where the internal pressure is still low, ambient air possibly enters the vial due to a pressure difference between the internal pressure of the vial and the atmospheric pressure, generating air bubbles in the medicinal solution in the vial. It is difficult and time-consuming to extract the medicinal solution alone from the medicinal solution containing the air bubbles, significantly increasing an operation time and thereby making the operation very inefficient.

A conventional means to avoid such an overly low internal pressure of the vial is to aspirate the medicinal solution from the vial into the syringe while gradually replacing the medicinal solution of the vial with the air inside the syringe. As illustrated in FIG. 15, air 103 is aspirated into a syringe 101 beforehand, and an injection needle 106 attached to the syringe 101 is then punctured into a rubber cap 107 which seals a vial 102 so that a needle tip reaches below the liquid surface of a medicinal solution 104 in the vial 102. After that, a piston 108 is moved in a direction where the piston is pulled out from an outer tube 109 to aspirate the medicinal solution 104 into the syringe 101. When it is determined that the internal pressure of the vial 102, which decreases as the medicinal solution 104 is aspirated, reaches a given value, a positional relationship between the vial 102 and the syringe 101 illustrated in FIG. 15 is reversed to be upside down so that the tip of the injection needle 106 is above the liquid surface of the medicinal solution 104. In the upside-down positioning, the piston 108 is moved in a direction where the piston is pushed into the outer tube 109 to transfer the air 103 in the syringe 101 alone into the vial 102 so that the internal pressure of the vial 102 is back to normal. When these steps are repeatedly performed, the medicinal solution 104 in the vial 102 can be aspirated into the syringe 101 with no sharp drop of the internal pressure of the vial 102.

In the case where the air is overly transferred from the syringe 101 into the vial 102, however, the internal pressure thereof increases over a regular pressure, exerting an action to make the vial 102 draw apart from the syringe 101. Such an overly high internal pressure of the vial 102 possibly causes the medicinal solution 104 to flow out from the high-pressure vial 102 into the atmosphere when the injection needle 106 is removed from the rubber cap 107 of the vial 102, which is generally called "aerosol phenomenon". The aerosol phenomenon is a factor which invites unfavorable events, for example, the medicinal solution 104 may be spilt around, the scattered medicinal solution 104 may be adhered to human body, and the vaporized medicinal solution 104 may be inhaled. To prevent such unfavorable events from happening in view of safety, it is necessary to completely avoid the aerosol phenomenon. Therefore, it is necessary to stop the transfer of the air from the syringe 101 before the internal pressure of the vial 102 becomes too high.

As described so far, the internal pressure of the vial needs to be properly adjusted to avoid an overly high or low internal pressure when the medicinal solution is aspirated from the vial, which is a medicinal solution container, into the syringe. The pressure adjustment should be similarly performed when the medicinal solution is injected from the syringe into the medicinal solution container. Conventionally, it solely relied upon the sensation felt with hands and visual confirmation by an operator who is holding a piston or a plunger to detect the internal pressure of the medicinal solution container. The operator has to manipulate the piston of the syringe while sensing the internal pressure of the medicinal solution container (from negative pressures to positive pressures), which requires a high level of concentration. In large healthcare facilities, for example, it is desirable that as many medication dispensing operations as possible be performed immediately before administering medications in order to improve a time efficiency and also promptly respond to any prescription changes. However, it is a very demanding task to perform the dispensing operation, which requires a high level of concentration, over long hours.

The Patent Document 1 discloses an infusion solution transfer device configured to move a piston provided in a syringe by applying a load thereto using a motor while detecting the internal pressure of the syringe to automatically transfer an infusion solution to a patient. The device developed to inject the liquid solution contained in the syringe into human body is, however, mostly used to check whether the solution is normally transferred. Therefore, the infusion solution transfer device disclosed in the Patent Document 1 can only detect the pressure when the piston is moved to be pushed in. The infusion solution transfer device disclosed in the Patent Document 1 is not configured to move the piston to be pulled out which is an indispensable operability in the dispensing operation or detect the internal pressure of a medicinal solution container when the piston is thus moved. During the described dispensing operation, the operator conventionally holds the syringe with one hand, while holding the medicinal solution container with the other hand. The device disclosed in the Patent Document 1 is a desktop device, which is not designed to be handled with hands. In view of at least these technical disadvantages, the device disclosed in the Patent Document 1 fails to teach any distinctive means effective for supporting the dispensing operation using the syringe.

Citation List

Patent Document

[Patent Document 1] Unexamined Japanese Patent Application Publication No. 05-42213

SUMMARY OF THE INVENTION

Technical Problem

The present invention provides a syringe drive device capable of effectively supporting a dispensing operation using a syringe. The present invention further provides a medication dispensing apparatus to which such a syringe drive apparatus is applied.

Solution Problem

A first aspect of the present invention provides a syringe drive device including: a syringe holding section configured to detachably hold an outer tube of a syringe; a piston manipulating section detachably engaged with a piston of the syringe having an end inserted in the outer tube; a piston drive section configured to move the piston manipulating section to thereby move the piston in a direction where the piston is pushed into the outer tube or a direction where the piston is pulled out from the outer tube; a piston controller configured to change a direction where the piston manipulating section is moved by the piston drive section; an internal pressure measuring section configured to measure an internal pressure of a medicinal solution container punctured with a needle attached to the outer tube of the syringe; and a display section configured to display the internal pressure of the medicinal solution container measured by the internal pressure measuring section.

A second aspect of the present invention provides a medication dispensing apparatus including: a syringe drive device holding section configured to detachably hold the syringe drive device; a container holding section configured to detachably hold the medicinal solution container; a movable section provided with the syringe drive device holding section on one end thereof and the container holding section on another end thereof, the movable section being configured to move the syringe drive device and the container holding section toward and away from each other; a pedestal section configured to rotatably support the movable section between the syringe drive device holding section and the container holding section; and a rotation drive section configured to rotate the movable section at a first position at which the syringe drive device holding section is positioned on a lower side and the container holding section is positioned on an upper side, and a second position at which the container holding section is positioned on the upper side and the syringe drive device is positioned on the lower side.

Effect of the Invention

An operator who uses the syringe drive device according to the present invention holds a grip portion with one hand to hold the syringe drive device mounted with the syringe. Then, the operator is able to move the syringe piston in the direction where the piston is pushed in or pulled out by inputting an instruction to an instruction input section while holding the syringe drive device. Simply by inputting an instruction whatever necessary to the instruction input section while holding the syringe drive device mounted with the syringe with one hand, the operator can easily aspirate the medicinal solution or air from the medicinal solution container into the syringe or inject the medicinal solution or air from the syringe into the medicinal solution container. This technical advantage of the syringe drive device according to the present invention exerts a remarkable operability in a medication dispensing operation such as mixing medication ingredients. Further, the internal pressure of the medicinal solution container measured by an internal pressure gauge is displayed on the display section. The operator who dispenses the medication can input an instruction to the instruction input section to move the piston in the direction where the piston is pushed in or pulled out while checking the internal pressure displayed on the display section. This technical advantage enables the operator to aspirate or inject the medicinal solution reliably and readily between the medicinal solution container and the syringe without overly decreasing or increasing the internal pressure of the medicinal solution container. The syringe drive device according to the present invention can effectively support the operator who dispenses the medication such as mixing medication ingredients.

DESCRIPTION OF THE EMBODIMENTS

Figure 1:
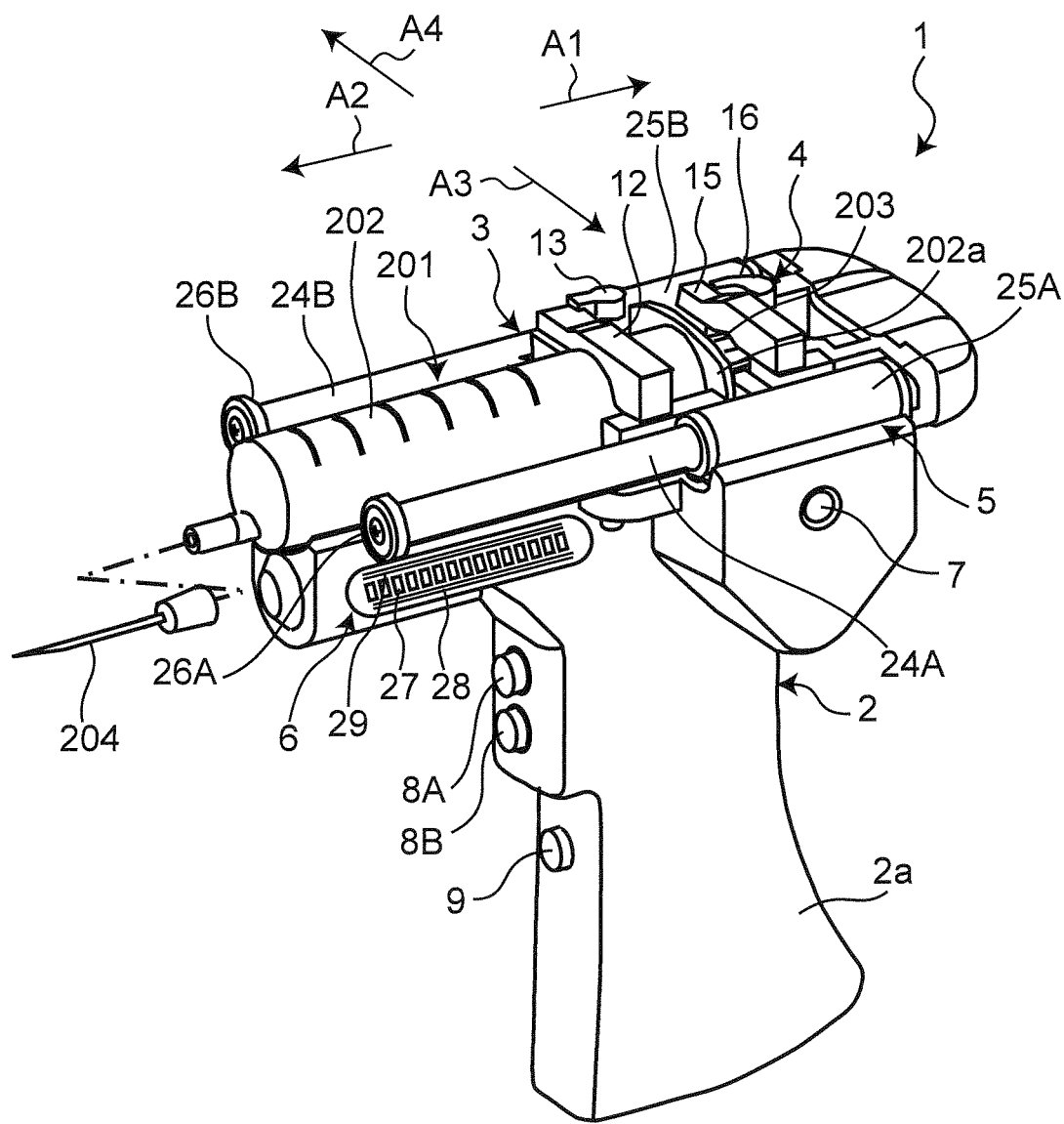
FIG. 1 is a perspective view of a syringe drive device according to an embodiment 1 of the present invention mounted with a syringe.

Hereinafter, embodiments of the present invention are described referring to the accompanied drawings. The same structural elements are simply illustrated with the same reference numerals to omit redundant description.

Embodiment 1

Figure 2:
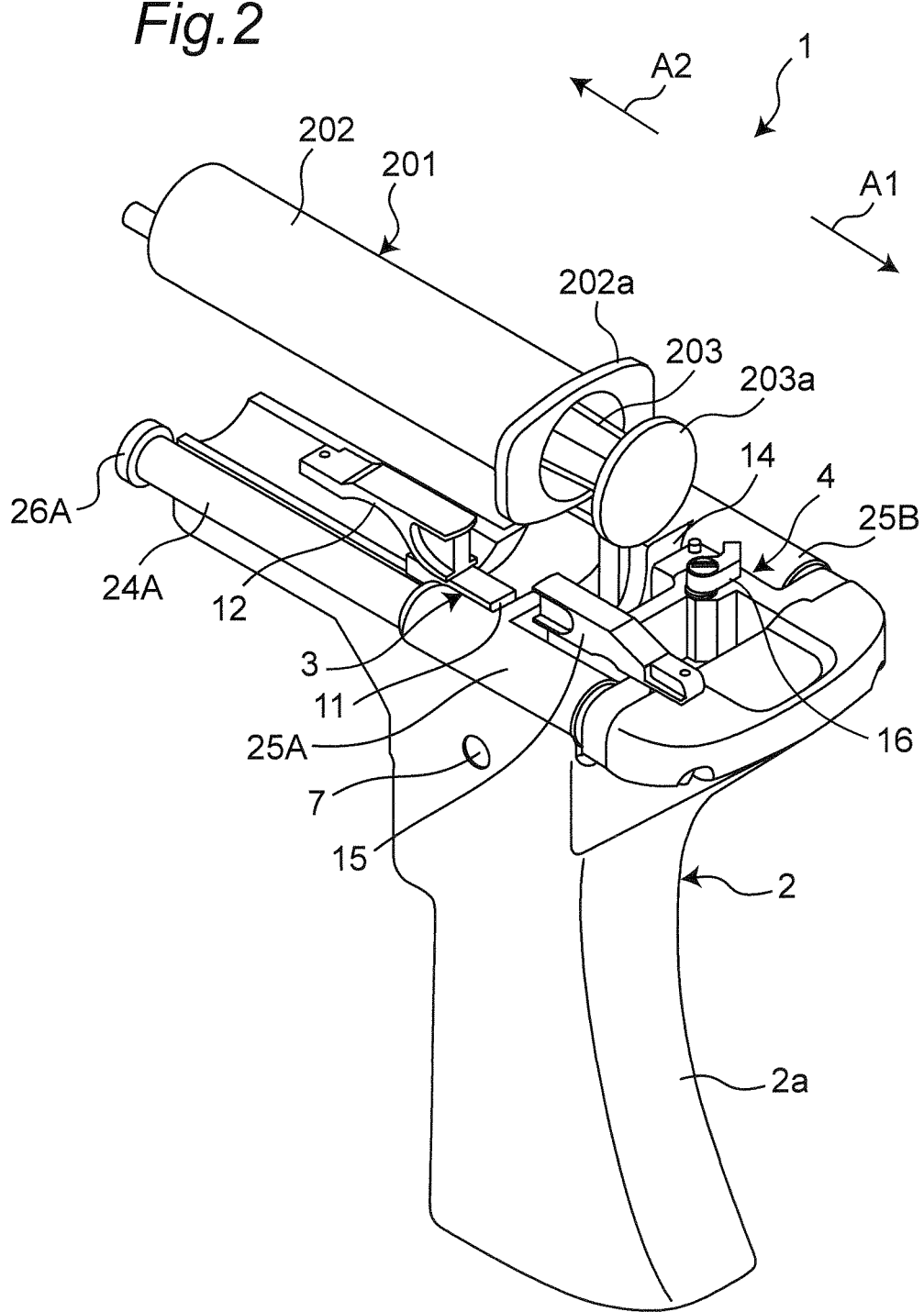
FIG. 2 is a perspective view of the syringe drive device according to the embodiment 1 from which the syringe is removed.

FIGS. 1 and 2 are perspective views of a syringe drive device 1 according to an embodiment 1 of the present invention. The syringe drive device 1 is designed to support an operator who dispenses a medication using a syringe 201. An example of the medication dispensing operation is a mixing operation to prepare, for example, an injection solution or an intravenous solution. Examples of the medication dispensing operation according to the present embodiment are; aspirating a medicinal solution from a vial 301 (see FIGS. 8A and 8B) which is a medicinal solution container into a syringe 201, and injecting a medicinal solution from the syringe 201 into the vial 301. The syringe 201 is provided with an outer tube 202 mounted with an injection needle 204 on an edge thereof, and a piston 203, an edge of which provided with a gasket (not illustrated in the drawing) is inserted in the outer tube 202 through an opening on the opposite side of the injection needle 204. A flange portion 202a is provided on an opening end of the outer tube 202, and a jaw portion 203a is provided on a rear end of the piston 203.

When the syringe drive device 1 is used, the injection needle 204 attached to the syringe 201 is punctured into a rubber cap 302 of the vial 301 so that the inside of the syringe 201 and the vial 301 form an enclosed space with no leak of air therefrom. The syringe 201 and the vial 301 form an enclosed space through the injection needle 204. Therefore, the syringe 201 and the vial 301 according to the present embodiment have an equal internal pressure. The description of the present embodiment is given based on that the syringe 201 and the vial 301 have an equal internal pressure. When the internal pressure of the vial 301 which forms the enclosed space as well as the syringe 201 increases over a regular pressure, there is a risk of leaking the medicinal solution and the vaporized medicinal solution to the outside when the injection needle 204 is removed from the rubber cap 302. When the internal pressure (negative pressure) of the vial 301 is overly low, on the other hand, there is a risk of bubble generation of a medicinal solution 303 contained in the vial 301 when the injection needle 204 is removed from the rubber cap 302. The present embodiment defines that an appropriate range of the internal pressure of the vial 301 in a steady state at which the injection needle 204 attached to the syringe 201 can be safely removed from the rubber cap 302 without causing these unfavorable events is −20 kPa to 0 kPa, expressed in gauge pressure. The specific numeral values of the upper and lower limits in the appropriate range can be differently set depending on the type of the medicinal solution, the type and capacity of the medicinal solution container, and environmental conditions during the operation such as temperature and atmospheric pressure.

The syringe drive device 1 has the features briefly described below. When an operation button 8A is pressed, the piston 203 can be automatically moved in a direction where the piston is pushed into the outer tube 202. When an operation button 8B is pressed, the piston 203 can be automatically moved in a direction where the piston is pulled out from the outer tube 202. A drive current supplied to a motor 17 (for example, see FIG. 3) which is a piston drive power source during the movement of the piston 203, and the internal pressure of the vial 301 while the piston 203 is at halt can be measured. The drive current supplied to the motor 17 and the internal pressure of the vial 301 can be displayed on a display section 6 to be visually confirmed. When the internal pressure of the vial 301 or the drive current supplied to the motor 17 overly increases or decreases, an alarm is outputted. Specific examples of the alarm are; sound, vibration, emission of light, and forced stop of the moving piston 203. When an internal pressure adjustment button 9 is pressed, the internal pressure of the vial 301 is automatically adjusted to stay in the appropriate range.

Hereinafter, the syringe drive device 1 according to the present embodiment is described in detail. In the description given below, left side of the syringe drive device 1 on the drawing of FIG. 1 may be called front side (side illustrated with arrow A2), right side thereof may be called rear side (side illustrated with arrow A1), near side thereof may be called left side (side illustrated with arrow A3), and far side thereof may be called right side (side illustrated with arrow A4).

As illustrated in FIGS. 1 and 2, a syringe holding section 3 which detachably holds the outer tube 202 of the syringe 201 is provided in an upper part of a body 2 of the syringe drive device 1, and a piston manipulating section 4 which is detachably engaged with the jaw portion 203a of the piston 203 of the syringe 201 is provided behind the syringe holding section 3. The body 2 is provided with a piston drive section 5 which moves the piston manipulating section 4 to thereby move the piston 203 in the direction where the piston is pushed into or pulled out from the outer tube 202. On the left side of the upper part of the body 2 are provided a display section 6 which displays at least one of the internal pressure of the vial 301 and the drive current of the motor 17, and a light-emitting section 7 which emits a blinking light in response to reception of an alarm signal.

A grip portion 2a which can be gripped by an operator with one hand is provided on a lower side of the body 2 of the syringe drive device 1. The grip portion 2a extends in a direction substantially orthogonal to the longitudinal direction of the outer tube 202 of the syringe 201 held by the syringe holding section 3. On the front side of the grip portion 2a are provided operation buttons 8A and 8B which are instruction input sections, and an internal pressure adjustment button 9. According to the present embodiment, the operation buttons 8A and 8B and the internal pressure adjustment button 9 are push-buttons where they become an on state when pressed by finger but they become an off-state when the finger is removed. As far as any instructions necessary can be manually inputted, structural and functional characteristics of the instruction input sections are not necessarily limited.

Referring to FIGS. 1 and 2, the syringe holding section 3 has a groove 11 into which the flange portion 202a of the outer tube 202 is fitted, and a seizing piece 12 provided at a position closer to the front side of the groove 11. The groove 11 secures a longitudinal position of the outer tube 202. The seizing piece 12 can rotate to and from a closing position illustrated in FIG. 1 and an open position illustrated in FIG. 2. When engaged with a locking claw 13 at the closing position, the seizing piece 12 is retained with pushing the outer tube 202. When the seizing piece 12 is disengaged from the locking claw 13 to rotate to the open position, the outer tube 202 can be removed from the syringe holding section 3. The piston manipulating section 4 has a groove 14 into which the jaw portion 203a of the piston 203 is fitted. At a position closer to the front side of the groove 14, the piston manipulating section 4 has a coupling piece 15 rotatable to and from a closing position illustrated in FIG. 1 and an open position illustrated in FIG. 2. When the coupling piece 15 at the closing position is engaged with a locking claw 16 while the jaw portion 203a of the piston 203 stays fitted in the groove 14, the piston 203 is coupled with the piston manipulating section 4. When the coupling piece 15 is disengaged from the locking claw 16 to rotate to the open position, the jaw portion 203a can be removed from the groove 14 so that the piston 203 and the piston manipulating section 4 can be decoupled from each other.

Figure 3:
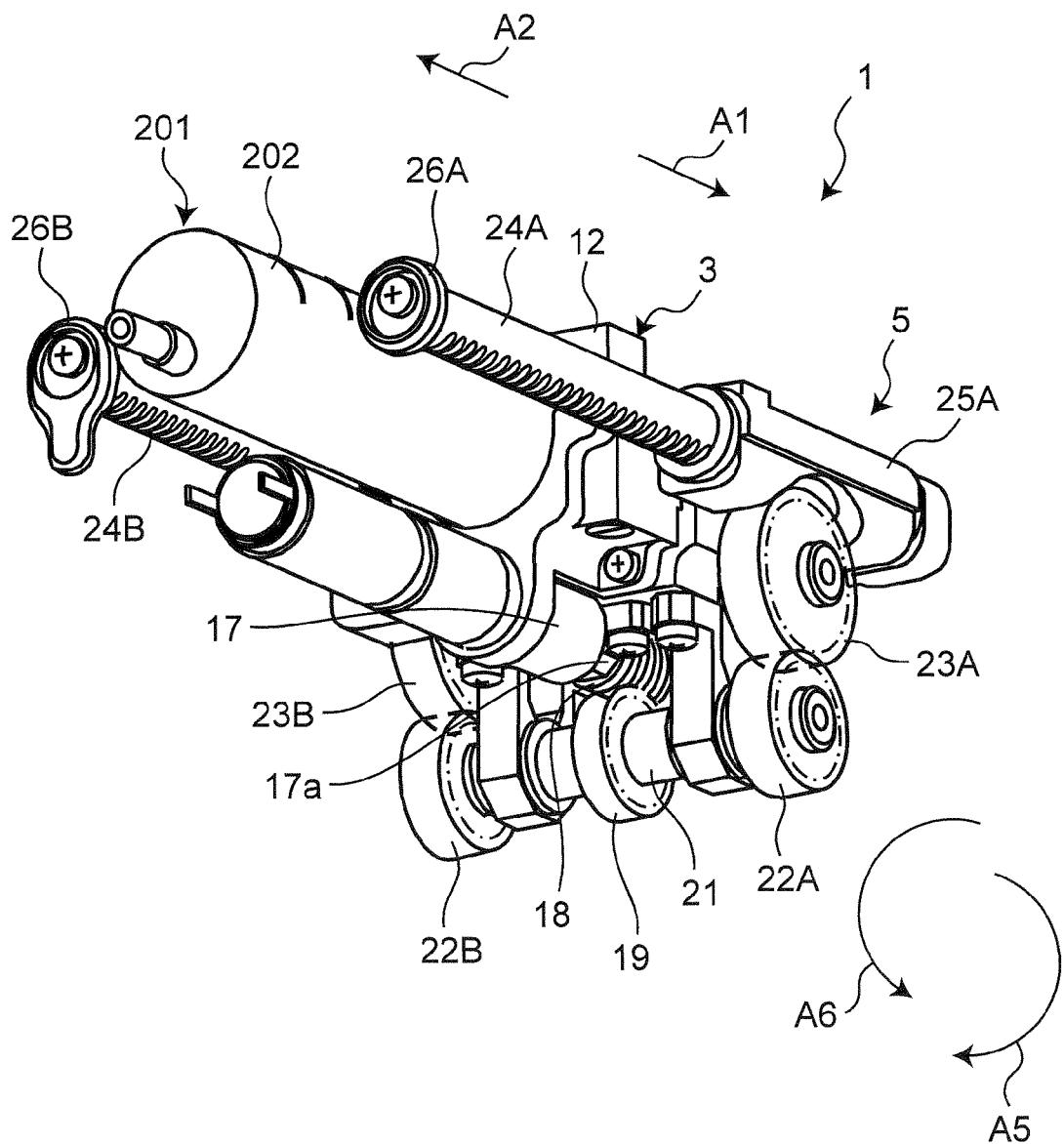
FIG. 3 is a perspective view of a piston drive section according to the embodiment 1 when viewed from below.
Figure 4:
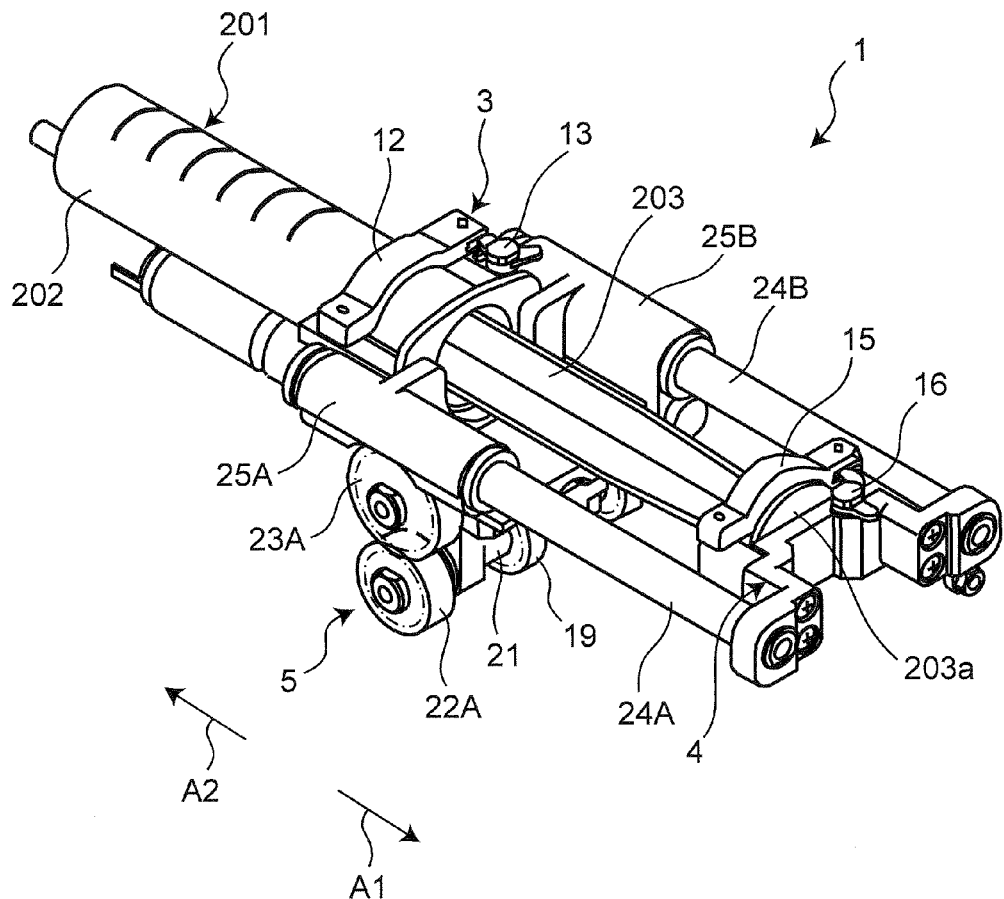
FIG. 4 is a perspective view of the piston drive section according to the embodiment 1 when viewed from above.

FIGS. 3 and 4 are drawings of the piston drive section 5 after the body 2 is removed from the syringe drive device 1, further illustrating the piston drive section 4, syringe 201, and syringe holding section 3. The piston drive section 5 has a motor 17 situated so that an output shaft 17a extends in the longitudinal direction of the syringe 201. The rotation of the motor 17 is transmitted from a worm gear 18 secured to the output shaft 17a to a gear 19, and further transmitted to gears 23A and 23B by way of left and right gears 22A and 22B secured to a common shaft 21 with the gear 19. A pair of racks 24A and 24B, which are straight cylindrical rods having lower surfaces notched at intervals, are provided in parallel with each other on the left and right of the outer tube 202 of the syringe 201 held by the syringe holding section 3. The racks 24A and 24B are supported by cylindrical bearings 25A and 25B respectively having open ends on both sides so as move straight along the longitudinal direction of the syringe 201 held by the syringe holding section 3. The rear ends of the racks 24A and 24B are coupled with the piston manipulating section 4, and edges thereof are provided with fall-out preventing members 26A and 26B. The gears 23A and 23B are engaged with the racks 24A and 24B via dented portions provided on lower parts of the bearings 25A and 25B. The rotation of the gears 23A and 23B transmitted from the motor 17 makes the racks 24A and 24B linearly move. When the racks 24A and 24B are moving, the piston 203 of the syringe 201 coupled with the racks 24A and 24B via the piston manipulating section 4 moves in a direction where the piston is pushed into or pulled out from the outer tube 202.

According to the present embodiment, when the motor 17 is reversely rotated, the gears 23A and 23B are rotated clockwise (direction illustrated with arrow A5) in FIGS. 3 and 4. Then, the racks 24A and 24B move the piston manipulating section 4 in the direction where the piston 203 of the syringe 201 is pulled out from the outer tube 202 as illustrated with arrow A1. When the motor 17 is normally rotated, the gears 23A and 23B are rotated anticlockwise (direction illustrated with arrow A6) in FIGS. 3 and 4. Then, the racks 24A and 24B move the piston manipulating section 4 in the direction where the piston 203 is pushed into the outer tube 202 as illustrated with arrow A2.

As illustrated in FIG. 1, the display section 6 is provided at a position near the syringe 201 held by the syringe holding section 3 on a side surface (left side) of the body 2 of the syringe drive device 1. The display section 6 is provided at such a position because an operator can watch a display thereon while checking an amount of medicinal solution in the syringe 201.

Figure 5:
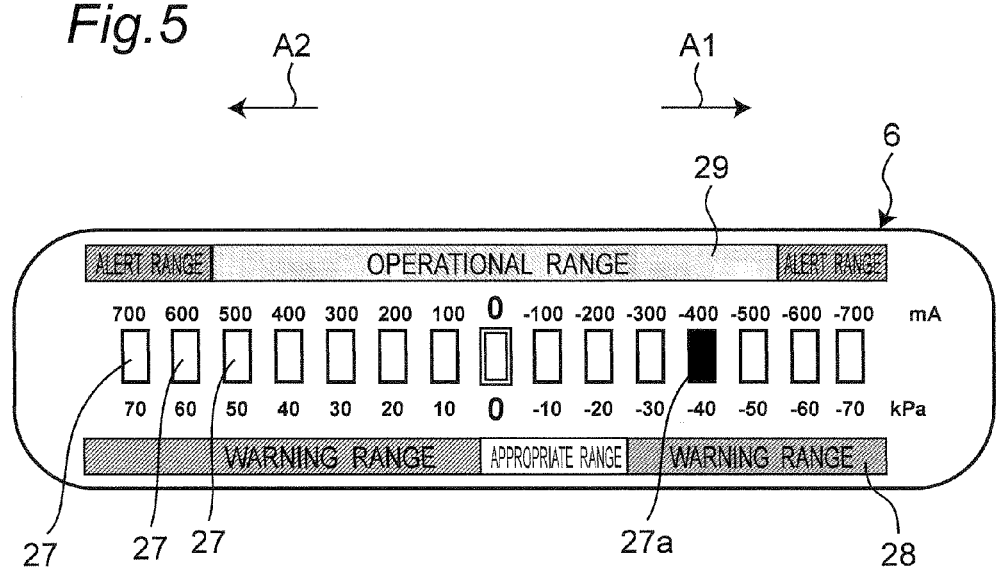
FIG. 5 is a front view of a display section according to the embodiment 1.

The display section 6 displays thereon one of a measured value of the internal pressure of the vial 301 and a detected value of the drive current of the motor 17 depending on an operation status of the syringe drive device 1 at the time (more specifically, statuses of the operation buttons 8A and 8B). Referring to FIGS. 1 and 5, the display section 6 has a plurality of light-emitting devices 27 linearly aligned in parallel with the moving direction of the piston 203 of the syringe 201 held by the syringe holding section 3. The light-emitting device 27 includes, for example, LED. Referring to FIG. 5, an internal pressure display lamp 28 and a current display lamp 29 both extending in a thin band shape are provided on the lower and upper sides of a row of light-emitting devices 27.

When the display section 6 displays the internal pressure of the vial 301, any of the light-emitting devices 27 emit light depending on the measured value of the internal pressure of the vial 301, and the internal pressure display lamp 28 is lighted on. The display section 6 according to the present embodiment can display the internal pressure values in the range of −70 kPa to 70 kPa including the appropriate range (−20 kPa to 0 kPa) on the row of light-emitting devices 27.

In the plurality of light-emitting devices 27, the direction where the piston 203 is pushed into the outer tube 202 (direction illustrated with arrow A2) is set as a positive pressure side, while the direction where the piston 203 is pulled out from the outer tube 202 (direction illustrated with arrow A1) is set as a negative pressure side. When, for example, the light-emitting device illustrated with a reference symbol 27a in FIG. 5 emits light, the measured internal pressure of the vial 301 is approximately −40 kPa. As the measured internal pressure value of the vial 301 increases, the position of the light-emitting device 27a which emits light shifts in the direction of arrow A2 (to left in FIG. 5). As the measured internal pressure value of the vial 301 decreases, the position of the light-emitting device 27a which emits light shifts in the direction of arrow A1 (to right in FIG. 5). Thus, the push-in or pull-out direction of the piston 203 is consistent with the direction where the internal pressure displayed by the light-emitting device 27 positionally shifts as the internal pressure increases or decreases. Therefore, the internal pressure of the vial 301 is displayed in a manner similar to the sensation felt with the operator's finger when the piston 203 is manually moved. The operator can instinctively recognize the internal pressure of the vial 301 displayed on the display section 6.

The internal pressure display lamp 28 shows an internal pressure appropriate range (−20 kPa to 0 kPa), a warning range equal to or larger than a positive pressure upper limit (0 kPa) of the internal pressure appropriate range, and a warning range equal to or smaller than a negative pressure lower limit (−20 kPa) of the internal pressure appropriate range. When the operator visually checks which of the three different ranges is represented by the light-emitting device 27 that emits light, whether the internal pressure of the vial 301 is appropriate, too high, or too low can be speedily determined.

When the display section 6 displays thereon the drive current of the motor 17, any of the light-emitting devices 27 emit light depending on the detected value of the drive current, and the current display lamp 29 is lighted on. The display section 6 according to the present embodiment can display on the row of light-emitting devices 27 the drive current in the range of −700 mA to 700 mA including an appropriate operational range, i.e., the range −500 mA to 500 mA, of the motor 17. Describing the positive and negative values of the drive current, positive current represents electric current which normally rotates the motor 17 (current of the motor 17 when the piston 203 is pushed into the outer tube 202 in the direction of arrow A2), and negative current represents electric current which reversely rotates the motor 17 (current of the motor 17 when the piston 203 is pulled out from the outer tube 202 in the direction of arrow A1).

In the plurality of light-emitting devices 27, an electric current which drives the motor 17 in the direction where the piston 203 is pushed into the outer tube 202 (direction illustrated with arrow A2) is set at positive current side, while an electric current which drives the motor 17 in the direction where the piston 203 is pulled out from the outer tube 202 (direction illustrated with arrow A1) is set at negative current side. When, for example, the light-emitting device illustrated with the reference symbol 27a in FIG. 5 emits light, the measured drive current of the motor 17 is approximately −400 mA. As the detected value of the drive current decreases toward zero, the position of the light-emitting device 27a which emits light shifts in the direction of arrow A2 (left side in FIG. 5). On the contrary, as the detected value of the drive current increases in the negative direction, the position of the light-emitting device 27a which emits light shifts in the direction of arrow A1 (to right in FIG. 5). This shows that: as the positive drive current is larger, the piston drive section 5 which uses the motor 17 as a power source pushes the piston 203 with a larger force; as the negative drive current is larger, the piston drive section 5 pulls out the piston 203 with a larger force. Thus, the direction where the piston 203 is pushed into or pulled out from the outer tube 202 is consistent with the direction where the emitting position of the light-emitting device 27 changes in accordance with the change of the drive current. Therefore, the drive current is displayed in a manner similar to the sensation felt with an operator's finger when the piston 203 is manually moved. The operator can instinctively recognize the internal pressure of the vial 301 displayed on the display section 6, achieving a remarkable operability.

The current display lamp 29 shows an appropriate operational range of the drive current of the motor 17 (−500 to 500 mA according to the present embodiment), an alert range equal to or larger than an upper limit (500 mA according to the present embodiment) of the appropriate operational range of the drive current of the motor 17, and an alert range equal to or smaller than a lower limit (−500 mA according to the present embodiment) of the appropriate operational range of the drive current of the motor 17. When the operator visually checks which of the three different ranges is represented by the light-emitting device 27 currently emitting light, whether the drive current is appropriate can be determined.

As described later, whether the display section 6 displays thereon the drive current of the motor 17 or the internal pressure of the vial 301 is decided depending on the status of the operation button 8A, 8B. When either of the operation button 8A or 8B is in the off state (Step S03, S09 in FIG. 7A), the current display lamp 29 emits light, and the detected drive current of the motor 17 is displayed by the display device 27. When neither of the operation button 8A nor 8B is pressed, the internal pressure display lamp 28 emits light, and the detected internal pressure is displayed by the display device 27.

By arranging the light-emitting devices 27 to emit lights respectively in different colors, the internal pressure of the vial 301 and the drive current of the motor 17 can be displayed on the display section 6 such that they can be more instinctively recognized. For example, the light-emitting devices 27 which indicate the appropriate range of the internal pressure of the vial 301 (−20 kPa to 0 kPa) emit green lights, while the light-emitting devices 27 which indicate two warning ranges emit yellow lights. In place of or in combination with the light-emitting devices such as LED, digital numerals may be used to display the values of the internal pressure of the vial 301 and the drive current of the motor 17.

To be able to visually check the display section 6 regardless of which of the operator's right and left hands is used to hold the grip portion 2a, the display section 6 provided on the left-side surface of the body 2 alone in the illustration of FIG. 1 is preferably provided on the right-side surface of the body 2 as well. In that case, the right and left sides of the display section 6 are preferably opposite to the illustration of FIG. 5 (positive and negative sides are reversed) so that the moving direction of the piston 203 is consistent with the direction where the displayed internal pressure of the vial 301 and drive current of the motor 17 change.

Figure 6:
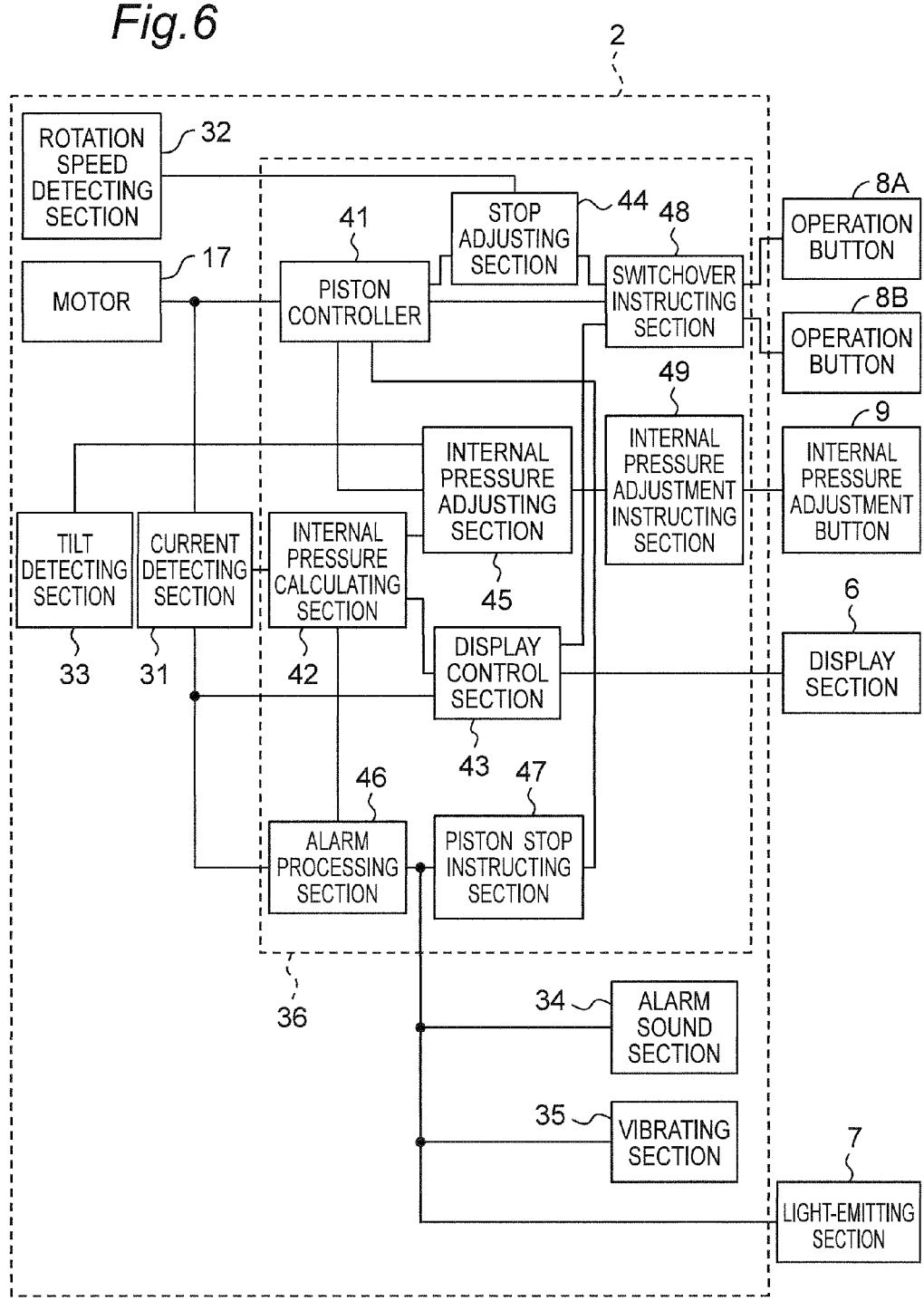
FIG. 6 is a control block diagram of the syringe drive device according to the embodiment 1.

Referring to FIG. 6, the body 2 of the syringe drive device 1 is mounted with, in addition to the motor 17 (piston drive section 5), a current detecting section 31, a rotation speed detecting section 32, a tilt detecting section 33, an alarm sound section 34, an vibrating section 35, and a controller 36. The current detecting section 31 detects the drive current supplied to the motor 17. The rotation speed detecting section 32 detects the rotation speed of the motor 17. The tilt detecting section 33 has a tilt sensor to detect whether the syringe 201 loaded in the syringe holding section 3 is directed upward or downward. More specifically, the tilt detecting section 33 detects whether the tip of the injection needle 204 of the syringe 201 loaded in the syringe holding section 3 points to the direction of gravity relative to the horizontal direction (syringe 201 is directed downward) or a direction opposite to the direction of gravity relative to the horizontal direction (syringe 201 is directed upward). The alarm sound section 34 generates an alarm sound such as beep sound. The vibrating section 35 generates vibration using a vibration source such as a vibration motor. The controller 36 controls the motor 17, display section 6, light-emitting section 7, alarm sound section 34, and vibrating section 35 based on the operator's instruction on whether the operation button 8A, 8B, or the internal pressure adjustment button 9 is pressed, and inputs from the current detecting section 31, rotation speed detecting section 32, and tilt detecting section 33.

The controller 36 includes a piston controller 41, an internal pressure calculating section 42, a display control section 43, a stop adjusting section 44, an internal pressure adjusting section 45, an alarm processing section 46, a piston stop instructing section 47, a switchover instructing section 48, and an internal pressure adjustment instructing section 49.

The piston controller 41 switches the positive or negative value of the drive current supplied to the motor 17 provided in the piston drive section 5 to thereby control the direction where the piston 203 is moved by the piston manipulating section 4. The piston controller 41 adjusts the current value of the drive current which drives the motor 17 to thereby control a driving force by which the piston 203 is moved in the push-in direction or the pull-out direction.

The internal pressure calculating section 42 calculates the internal pressure of the vial 301 (from negative pressure range to positive pressure range) punctured with the injection needle 204 attached to the syringe 201 based on the drive current of the motor 17 detected by the current detecting section 31. According to the present embodiment, the current detecting section 31 and the internal pressure calculating section 42 constitute the internal pressure measuring section.

The display control section 43 controls the display section 6 so that the drive current of the motor 17 detected by the current detecting section 31 and the internal pressure of the vial 301 calculated by the internal pressure calculating section 42 are displayed in the described manner.

The stop adjusting section 44 performs feedback control of the drive current supplied to the motor 17 using the piston controller 41 so that the rotation speed of the motor 17 detected by the rotation speed detecting section 32 is zero.

The internal pressure adjusting section 45 outputs an instruction on the positive or negative value and the current value of the drive current of the motor 17 to the piston controller 41 so that the internal pressure of the vial 301 stays in the appropriate range.

The alarm processing section 46 monitors the drive current of the motor 17 detected by the current detecting section 31 and the internal pressure of the vial 301 calculated by the internal pressure calculating section 42, and outputs an alarm signal depending on the monitored values to alarm devices of the light-emitting section 7, alarm sound section 34, vibrating section 35, and piston stop instructing section 47. The piston stop instructing section 47 outputs an instruction to stop the piston 203 to the piston controller 41.

The switchover instructing section 48 detects the status of the operation button 8A, 8B, that is whether the operation button 8A, 8B is pressed, and outputs instructions to the piston controller 41, display control section 43, and stop adjusting section 44.

When the internal pressure adjustment button 9 is pressed, the internal pressure adjustment instructing section 49 outputs an instruction to adjust the internal pressure to the internal pressure adjusting section 45.

Figure 7A:
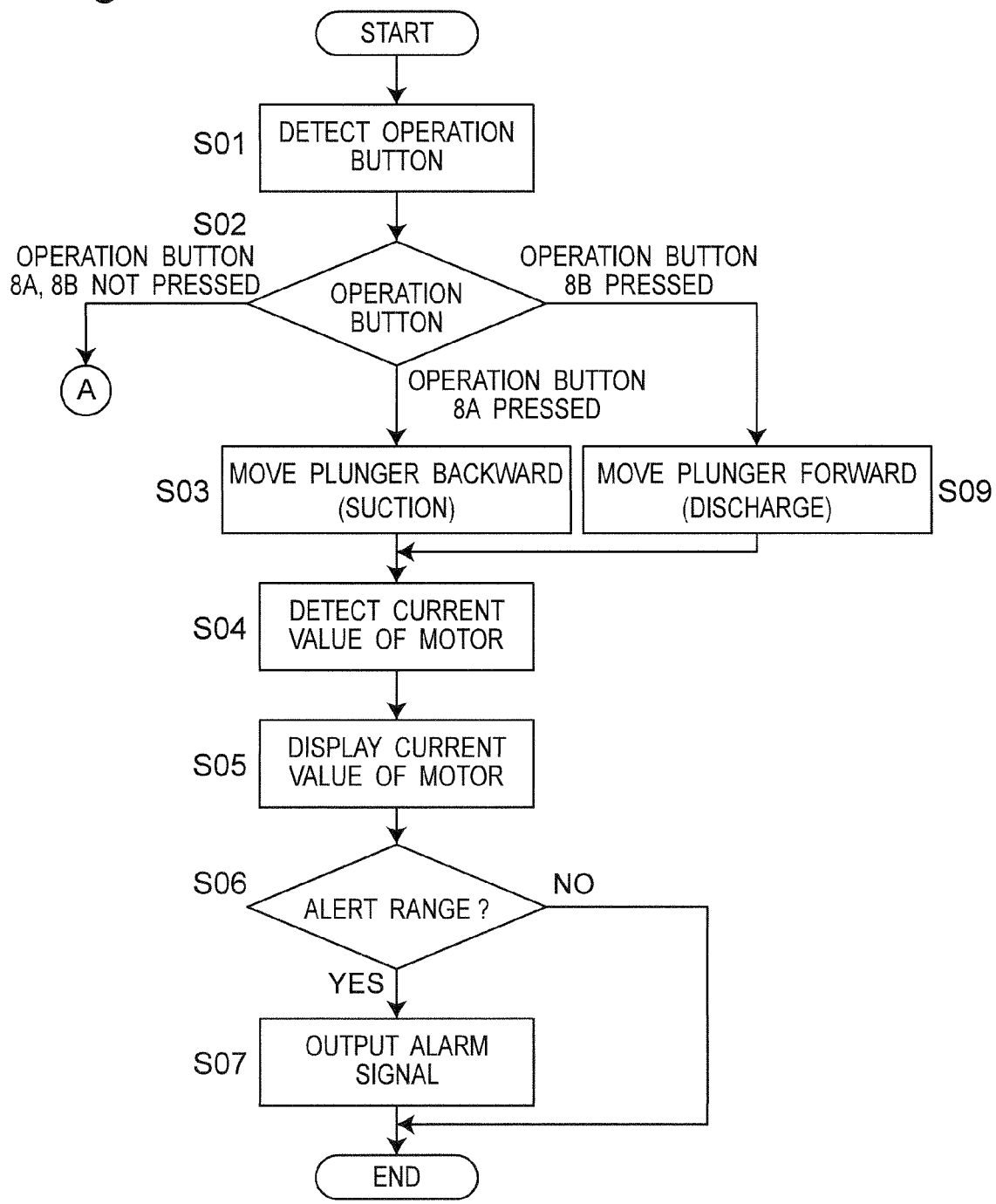
FIG. 7A is a flow chart illustrating processing steps in an operation of the syringe drive device according to the embodiment 1.
Figure 7B:
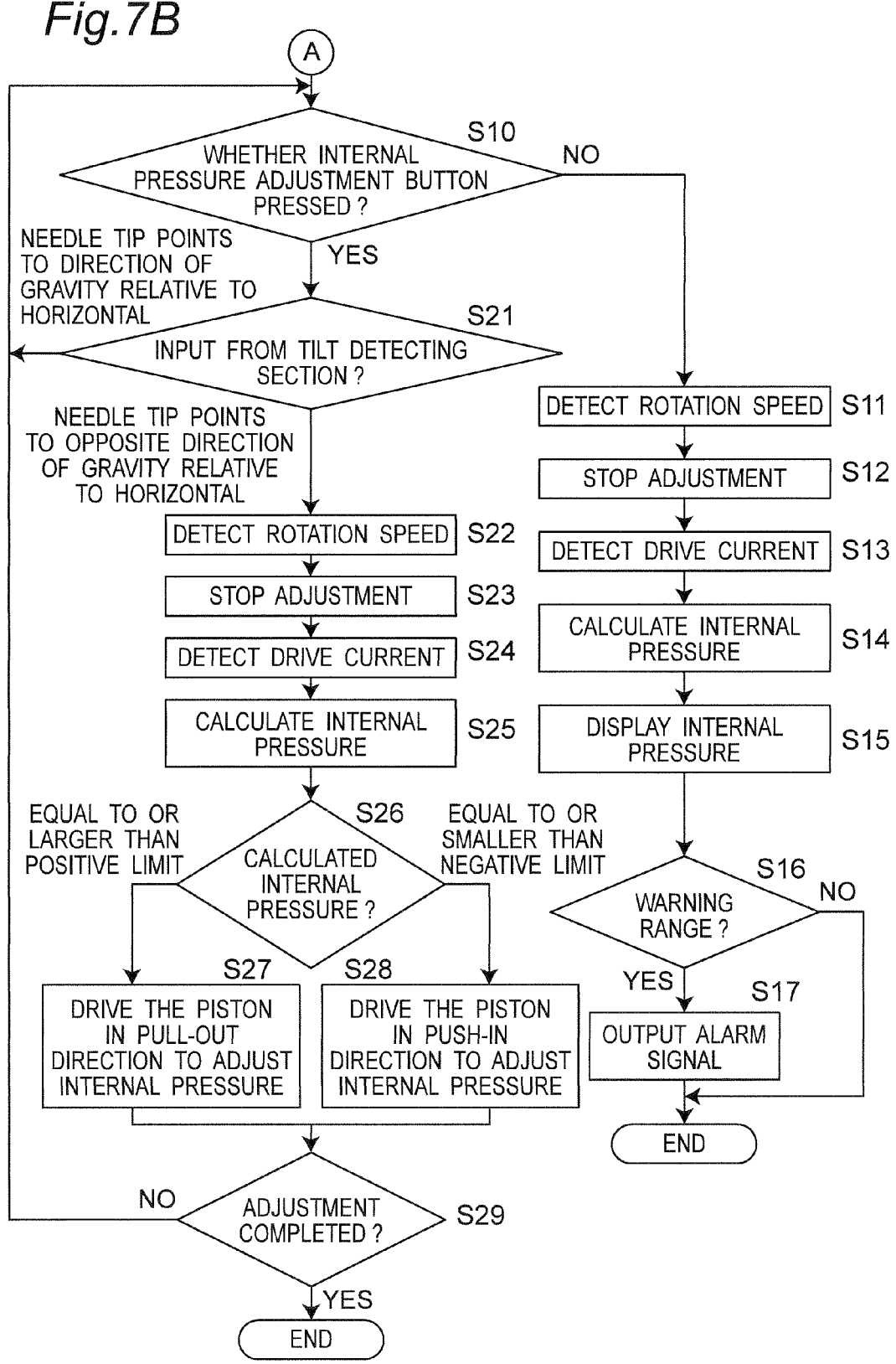
FIG. 7B is a flowchart illustrating the operation of the syringe drive device according to the embodiment 1.

Referring to flow charts illustrated in FIGS. 7A and 7B, the operation of the syringe drive device 1 is described. The flow charts illustrate the operation of the syringe drive device 1 after the outer tube 202 is mounted on the syringe holding section 3 to couple the piston 203 with the piston manipulating section 4, and the injection needle 204 attached to the syringe 201 is punctured into the rubber cap 302 of the vial 301.

In Step S01, the switchover instructing section 48 detects the status of the operation button 8A, 8B. When it is detected in Step S02 that the operation button 8A is ON state, the piston controller 41 supplies a negative drive current to the motor 17 as instructed by the switchover instructing section 48. The piston manipulating section 4 driven by the piston drive section 5 moves the piston 203 in the pull-out direction illustrated with arrow A1 (Step S03). When it is detected in Step S02 by the switchover instructing section 48 that the operation button 8B is ON state, the piston controller 41 supplies a positive drive current to the motor 17 as instructed by the switchover instructing section 48. The piston manipulating section 4 driven by the piston drive section 5 moves the piston 203 in the push-in direction illustrated with arrow A2.

In Step S04, the current detecting section 31 detects the direction and intensity of the drive current supplied to the motor 17. The detected direction and intensity of the drive current supplied to the motor 17 is displayed on the display section 6 by the display control section 43 (Step S05). While the piston manipulating section 4 is in action after the operation button 8A, 8B is pressed to supply the drive current to the motor 17, the drive current detected by the current detecting section 31 is displayed on the display section 6.

The direction and intensity of the drive current supplied to the motor 17 detected by the current detecting section 31 are also inputted to the alarm processing section 46. After detected in Step S06 that the drive current is in the alert range (500 mA to −500 mA according to the present embodiment), the alarm processing section 46 outputs an alarm signal in Step S07. When the alarm signal outputted by the alarm processing section 46 is received, at least one of the followings is carried out; alarm sound by the alarm sound section 34, vibration by the vibrating section 35, light emission by the light-emitting section 7, and forced stop of the moving piston 203. The forced stop of the moving piston 203 is carried out by the piston controller 41 instructed by the piston stop instructing section 47.

One or more of the alarm sound section 34, vibrating section 35, light-emitting section 7, and piston stop instructing section 47 may be put in action at the same time, or these structural elements may be put in action in different stages one after another. When, for example, the drive current of the motor 17 reached the alert range, to start with, the light-emitting section 7 is put in action to emit light (continuous light or blinking light). In the event of further change of the drive current of the motor 17 away from the operational range, the vibration by the vibrating section 35 and the alarm sound by the alarm sound section 34 are generated. In the case where the drive current of the motor 17 still continues to be further away from the operational range, the piston 203 is forced to stop by the piston stop instructing section 47. Thus, the drive current of the motor 17 is monitored while the piston 203 is being moved by the motor 17 in the push-in direction or the pull-out direction (during the aspirating or injection of the medicinal solution 303 or air to and from the vial 301), and the operator is warned or the piston 203 is forced to stop when the drive current is likely to exceed the largest allowable value, which prevents any overload on the motor 17, thereby improving the lifetime of the motor 17.

When the switchover instructing section 48 detects in Step S02 that the operation buttons 8A and 8B are both OFF state, the internal pressure adjustment instructing section 49 detects in Step S10 the status of the internal pressure adjustment button 9. When it is detected in Step S10 that the internal pressure adjustment button 9 is OFF state, various processes, including measuring the internal pressure of the vial 301, are carried out in Steps S11 to S17. When it is detected in Step S10 that the internal pressure adjustment button 9 is ON state, the internal pressure of the vial 301 is automatically adjusted in Steps S21 to S29.

Hereinafter, Steps S11 to S17 are described.

In Step S11, the rotation speed detecting section 32 detects the rotation speed of the motor 17. In Step S12, the stop adjusting section 44 performs feedback control of the drive current supplied to the motor 17 using the piston controller 41 so that the rotation speed detected by the rotation speed detecting section 32 is zero. The stop adjusting section 44 stops the movement of the piston manipulating section 4 (piston 203) against the internal pressure of the vial 301 to let the piston manipulating section 4 stay at this point.

In Step S13, the direction and intensity of the drive current when the rotation speed of the motor 17 is zero is detected by the current detecting section 31. In Step S14, the internal pressure calculating section 42 calculates the internal pressure of the vial 301 based on the drive current of the motor 17 detected by the current detecting section 31. The calculated internal pressure of the vial 310 is displayed on the display section 6 by the display control section 43 (Step S15). Therefore, the operator can visually check the internal pressure of the vial 301 in a state in which the injection needle 204 of the syringe 201 loaded in the syringe drive device 1 is still punctured.

The internal pressure of the vial 301 calculated by the internal pressure calculating section 42 is also inputted to the alarm processing section 46. After detected in Step S16 that the internal pressure of the vial 301 reached the warning range (equal to or larger than 0 kPa and equal to or smaller than −40 kPa according to the present embodiment), the alarm processing section 46 outputs an alarm signal in Step S16. When the alarm signal outputted by the alarm processing section 46 is received, at least one of the followings is carried out; alarm sound by the alarm sound section 34, vibration by the vibrating section 35, light emission by the light-emitting section 7, and forced stop of the moving piston 203. The forced stop of the moving piston 203 is carried out by the piston controller 41 instructed by the piston stop instructing section 47.

One or more of the alarm sound section 34, vibrating section 35, light-emitting section 7, and piston stop instructing section 47 may be put in action at the same time, or these structural elements may be put in action in different stages one after another. When, for example, the internal pressure of the vial 301 reached the warning range, the light-emitting section 7 is put in action to emit light first. In the event of further change of the internal pressure of the vial 301 away from the operational range, the vibration by the vibrating section 35 and the alarm sound by the alarm sound section 34 are generated. In the case where the internal pressure of the vial 301 still continues to be further away from the operational range, the piston 203 is forced to stop by the piston stop instructing section 47. Thus, the drive current of the motor 17 is monitored while the piston 3 is being moved by the motor 17 in the push-in direction or the pull-out direction (during the aspirating or injection of the medicinal solution 303 or air to and from the vial 301), and the operator is warned or the piston 203 is forced to stop when the drive current is likely to exceed the largest allowable value. This prevents any overload on the motor 17, thereby improving the lifetime of the motor 17. When the warning process is performed whenever the internal pressure of the vial 301 fails to stay in the appropriate range, the operator can know that a caution is needed when he or she removes the injection needle 204 from the vial 301.

Hereinafter is described the calculation of the internal pressure of the vial 301 by the internal pressure calculating section 33.

When the moving speed of the piston 203 is zero, it is unnecessary to take into account a viscosity resistance caused by the flowage of the medicinal solution 304 from the vial 301. This indicates that a reaction force against the internal pressure of the vial 301 from the piston manipulating section 4 acts on the piston 203. For example, the internal pressure of the vial 301 having a negative value exerts such an action that moves the piston 203 in the push-in direction. Therefore, the reaction force in the pull-out direction acts on the piston 203 as far as the moving speed is zero. For example, the internal pressure of the vial 301 having a positive value exerts such an action that moves the piston 203 in the pull-out direction. Therefore, the reaction force in the push-in direction acts on the piston 203 as far as the moving speed is zero. The reaction force against the internal pressure of the vial 301 from the piston manipulating section 4 acting on the piston 203 relies upon an output torque of the motor 17, and the output torque of the motor 17 is proportional to the drive current. Based on the analysis, the present embodiment uses the drive current when the rotation speed of the motor 17 is zero (when the moving speed of the piston 203 is zero), thereby eliminating any condition that complicates the calculation. As a result, the internal pressure of the vial 301 can be calculated under a simplified condition. The simplified condition that the calculation is performed when the moving speed of the piston 203 is zero makes it unnecessary to take into account the viscosity resistance caused by the flowage of the medicinal solution 303 from the vial 301, thereby realizing the estimation of the internal pressure of the vial 301. The viscosity resistance, which is decided by many factors such as conditions of wall surfaces and inner shapes of the syringe 201 and the injection needle 204, and viscosity of the medicinal solution 303 in the vial 301, is very difficult to estimate. Therefore, it is a great advantage to be able to disregard the viscosity resistance.

More specifically, as a result of the feedback control so that the rotation speed of the motor 17 is zero, a sum of the output torque of the motor 17 plus statical friction of the piston 203 and statical friction such as friction of a motor drive transmission mechanism balances out with the force acting on the piston 203 applied by the internal pressure of the vial 301. The internal pressure calculating section 42 takes into account the offset generated by these static frictions previously measured when the internal pressure of the vial 301 is calculated as described below. In the description below, the drive current value of the motor 17 when the moving speed of the piston 203 is zero is called I, and the internal pressure of the vial 301 is called P. When the measured drive current I has a positive value (the motor 17 is driven in normal rotational direction), the internal pressure P has a positive value, and the moving direction of the piston 203 moved by the piston manipulating section 4 is the push-in direction. Given that a constant of proportionality between the drive current I and an energizing force of the piston 203 moved by the piston manipulating section 4 is a, and the offset by the static frictions is b, a relationship expressed by P=aI−b is obtained. When the measured drive current I has a negative value (the motor 17 is driven in reversed rotational direction), the internal pressure P has a negative value, and the moving direction of the piston 203 moved by the piston manipulating section 4 is the pull-out direction, in which case P=aI+b. The internal pressure calculating section 42 calculates the internal pressure based on these relationships depending on the detected drive current.

Next, Steps S21 to S29 are described.

Figure 8A:
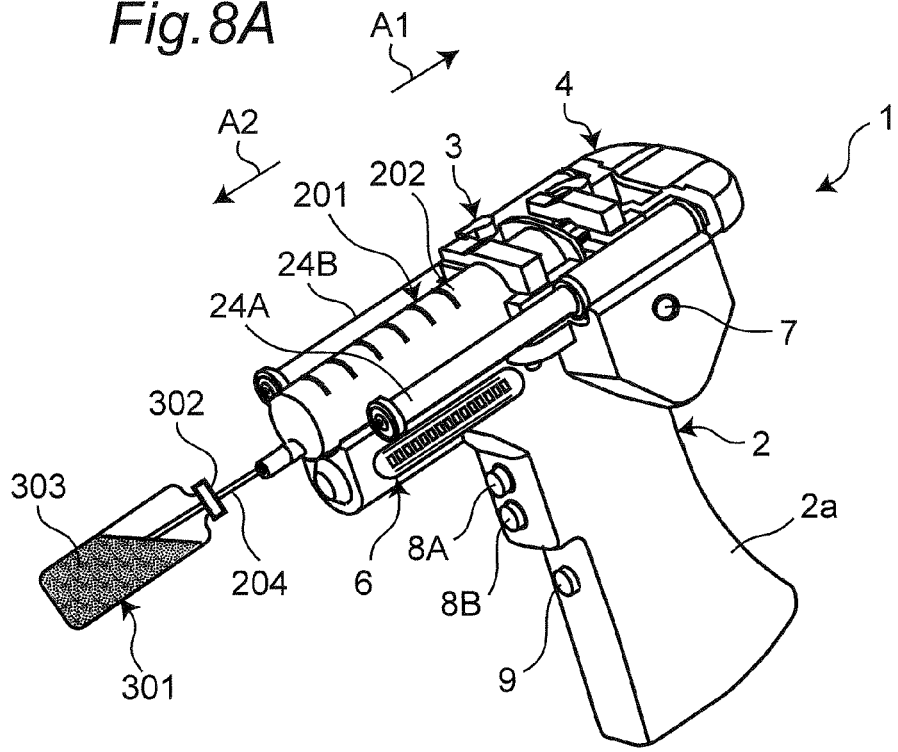
FIG. 8A is a perspective view of the syringe drive device according to the embodiment 1 which aspirates a medicinal solution into the syringe.
Figure 8B:
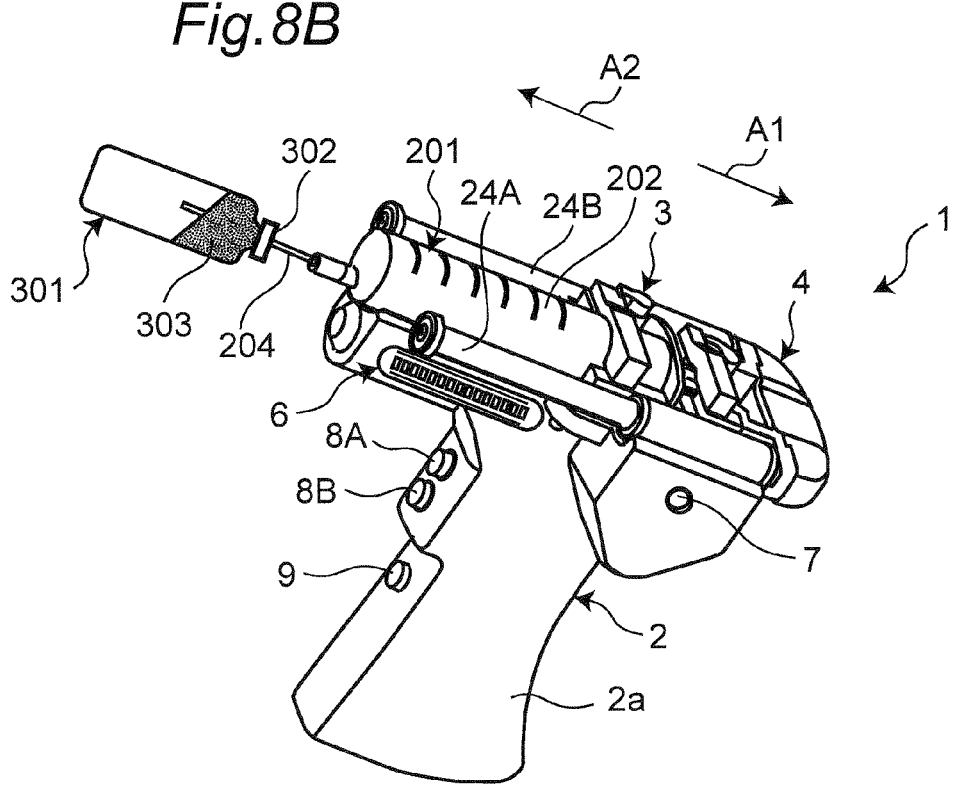
FIG. 8B is a perspective view of the syringe drive device according to the embodiment 1 when an internal pressure of the syringe is currently adjusted.

When the internal pressure adjustment instructing section 49 detects that the internal pressure adjustment button 9 is ON state (Step S10), the internal pressure adjustment instructing section 49 outputs an instruction to adjust the internal pressure to the internal pressure adjusting section 45. Based on the input from the tilt testing section 33, the internal pressure adjusting section 45 determines the direction of the injection needle 204 (Step S21). When, in Step S21, it is determined that that the tip of the injection needle 204 points to a direction opposite to the direction of gravity relative to the horizontal direction (for example, as illustrated in FIG. 8B), the internal pressure adjusting section 45 executes Steps S22 to S29 to automatically adjust the internal pressure of the vial 301. When it is determined that that the tip of the injection needle 204 points to the direction of gravity relative to the horizontal direction (for example, as illustrated in FIG. 8A), the internal pressure adjusting section 45 does not perform the automatic adjustment of the internal pressure of the vial 301. The internal pressure of the vial 301 is adjusted by aspirating or injecting air from the syringe 201 into the vial 301. Therefore, it is necessary that the tip of the injection needle 204 be directed upward and above the liquid surface of the medicinal solution 303. The internal pressure adjusting section 45 according to the present embodiment checks the direction of the injection needle 204, and determines that the tip of the injection needle is above the liquid surface of the medicinal solution 303 as far as the tip is directed upward, and then adjusts the internal pressure of the vial 301.

Steps S22 to S25 (control the drive current of the motor 17 so that the rotation speed is zero, detect the drive current of the motor 17, calculate the internal pressure of the vial 301) are similar to Steps S11 to S14 described earlier. When, in Step S26, it is determined that the internal pressure of the vial 301 calculated by the internal pressure calculating section 42 is equal to or larger than the positive pressure upper limit (0 kPa according to the present embodiment), the internal pressure adjusting section 45 requests the piston controller 41 to move the piston 203 in the pull-out direction (Step S27). After the piston 203 is moved in the pull-out direction as requested, the air in the vial 301 is aspirated into the syringe 201, and the internal pressure of the vial 301 is thereby reduced. When, in Step S26, it is determined that the internal pressure calculated by the internal pressure calculating section 42 is equal to or smaller than the negative pressure lower limit (−40 kPa according to the present embodiment), the internal pressure adjusting section 45 requests the piston controller 41 to move the piston 203 in the push-in direction (Step S28). After the piston 203 is moved in the push-in direction as requested, the air in the syringe 201 is injected into the vial 301, and the internal pressure of the vial 301 is thereby elevated. The processing steps described so far are repeated until the adjustment is completed (Step S29).

Hereinafter is described the operation for aspirating the medicinal solution 303 from the vial 301 into the syringe 201 using the syringe drive device 1. For example, the operator holds the grip portion 2a with his/her right hand like holding a gun. In this case, the operator can press any of the operation buttons 8A and 8B and the internal pressure adjustment button 9 with forefinger of his/her right hand like pulling a trigger without releasing his/her right hand from the grip portion 2a.

To be ready to aspirate the medicinal solution 303 in the vial 301 into the syringe 2, the operation button 8A is pressed with the tip of the injection needle 204 being exposed to atmosphere, so that an appropriate amount of air is aspirated into the syringe 201. When the operation button 8A is pressed, the motor 17 is reversely rotated, and the piston manipulating section 4 coupled with the racks 24A and 24B is moved backward by the rotation. Then, the piston 203 coupled with the piston manipulating section 4 is moved backward (pull-out direction), and the air is thereby aspirated into the syringe 201. As soon as the air slightly less than the medicinal solution to be aspirated is introduced into the syringe, the operator releases his/her hand from the operation button 8A to stop the aspirating.

Then, the operator holds the syringe drive device 1 mounted with the syringe 201 with one hand, and punctures the injection needle 204 of the syringe 201 into the rubber cap 302 of the vial 301 held with the other hand. When the injection needle 204 is thus punctured in the rubber cap 302, the syringe 201 and the vial 301 form an enclosed spaces with no leak of air therefrom. When, for example, the operator holds the grip portion 2a with his/her right hand, the injection needle 204 extends in substantially the same direction as his/her right forearm. Then, the operator can easily puncture the injection needle 204 of the syringe 201 into the rubber cap 302 of the vial 301 held with his/her left hand at a right position and a right angle.

As illustrated in FIG. 8A, the operator then changes the direction of the syringe drive device so that the 1 syringe 201 is directed downward and the injection needle 204 is below the liquid surface of the medicinal solution 303 in the vial 301. After that, the operator presses the operation button 8A of the syringe drive device 1 to move the piston manipulating section 4 backward. As a result, the piston 203 is moved in the pull-out direction, and the medicinal solution 303 in the vial 301 is aspirated into the syringe 201. As illustrated in FIG. 8B, the operator changes the direction of the syringe drive device 1 so that the syringe 201 is directed upward and the injection needle 204 is above the liquid surface of the medicinal solution 303 in the vial 301. After that, the operator presses the operation button 8B of the syringe drive device 1 to move the piston manipulating section 4 forward. As a result, the piston 203 is moved in the push-in direction, and the internal pressure of the vial 301 injected with the air from the syringe 201 is back to normal. By repeating these working steps, the medicinal solution 303 is aspirated from the vial 301 into the syringe 201 by replacing the medicinal solution 303 in the vial 301 with the air of the syringe 201.

Hereinafter is described the operation for injecting the medicinal solution from the syringe 201 into the vial 301 using the syringe drive device 1. First, the operator holds the syringe drive device 1 mounted with the syringe 201 with one hand, and punctures the injection needle 204 of the syringe 201 into the rubber cap 302 of the vial 301 held with the other hand in which a powdery medicinal agent is contained. When the injection needle 204 is thus punctured in the rubber cap 302, the syringe 201 and the vial 301 form an enclosed space with no leak of air therefrom.

The operator then presses the operation button 8B when the injection needle 204 of the syringe 201 is situated in air contained in the vial 301 (for example, see FIG. 8B). Then, the piston 203 is moved in the pull-out direction with the piston manipulating section 4, and air in the vial 301 is aspirated into the syringe 201. As a result, the internal pressure of the vial 301 slowly goes down. After the operator releases operator's finger from the operation button 8B to stop the movement of the piston 203, the operator changes the positional relationship between the vial 301 and the syringe 201 so that the medicinal solution is pushed out from the syringe 201 (for example, see FIG. 8A). In this state, the operator presses the operation button 8B. As a result, the piston 203 is moved in the push-in direction with the piston manipulating section 4, and the medicinal solution in the syringe 201 is injected into the vial 301. By repeating these working steps, the medicinal solution is injected from the syringe 201 into the vial 301 by replacing the air in the vial 301 with the medicinal solution in the syringe 201.

The syringe drive device 1 according to the present embodiment accomplishes the following technical advantages in aspirating and injecting the medicinal solution to and from the syringe 201 and the vial 301 as described so far. The syringe drive device 1 according to the present embodiment capable of achieving a remarkable operability can effectively support the operator.

When the syringe drive device 1 is held with one hand by gripping the grip portion 2a and the operation button 8A, 8B is simply pressed, the medicinal solution and the air can be easily aspirated and injected by moving the piston 203 of the syringe 201 in the push-in and pull-out directions both. Further, the operator can press any of the operation buttons 8A and 8B and the internal pressure adjustment button 9 with his/her forefinger on the front side of the grip portion 2a while holding the grip portion 2A with any other fingers except the forefinger. Therefore, the operator can manipulate the syringe drive device 1 without releasing one of his/her hands gripping the grip portion 2a or releasing the vial 301 held with the other hand.

During the aspirating or injection of the medicinal solution and air with the operation button 8A, 8B being pressed down, the drive current of the motor 17 detected by the current detecting section 31 is displayed on the display section 6. When neither of the operation button 8A nor 8B is pressed by the operator, the internal pressure of the vial 301 calculated by the internal pressure calculating section 42 is displayed on the display section 6. The operator, while checking the displayed values, tilts the syringe drive device 1 as illustrated in FIG. 8B whenever necessary and operates the operation button 8A, 8B so that the piston 203 is moved in the push-in direction or the pull-out direction by the piston manipulating section 4. Thus, the internal pressure of the vial 301 can be adjusted. When the syringe drive device 1 is tilted as illustrated in FIG. 8B and the internal pressure adjustment button 9 is pressed, the internal pressure of the vial 301 can be automatically adjusted to stay in the appropriate range. Because the internal pressure of the vial 301 can be thus readily adjusted, the internal pressure of the vial 301 is prevented from being overly high or low during the aspirating and injection of the medicinal solution to and from the vial 301 and the syringe 201. This successfully prevents the unfavorable events conventionally occurred; exposure of the medicinal solution or vaporized medicinal solution to outside of the vial when the needle is removed from the vial 301 having an overly high internal pressure, and generation of bubbles when the internal pressure is too low, thereby greatly helping the operator to perform the medication dispensing operation safely and easily.

Embodiment 2

Figure 9:
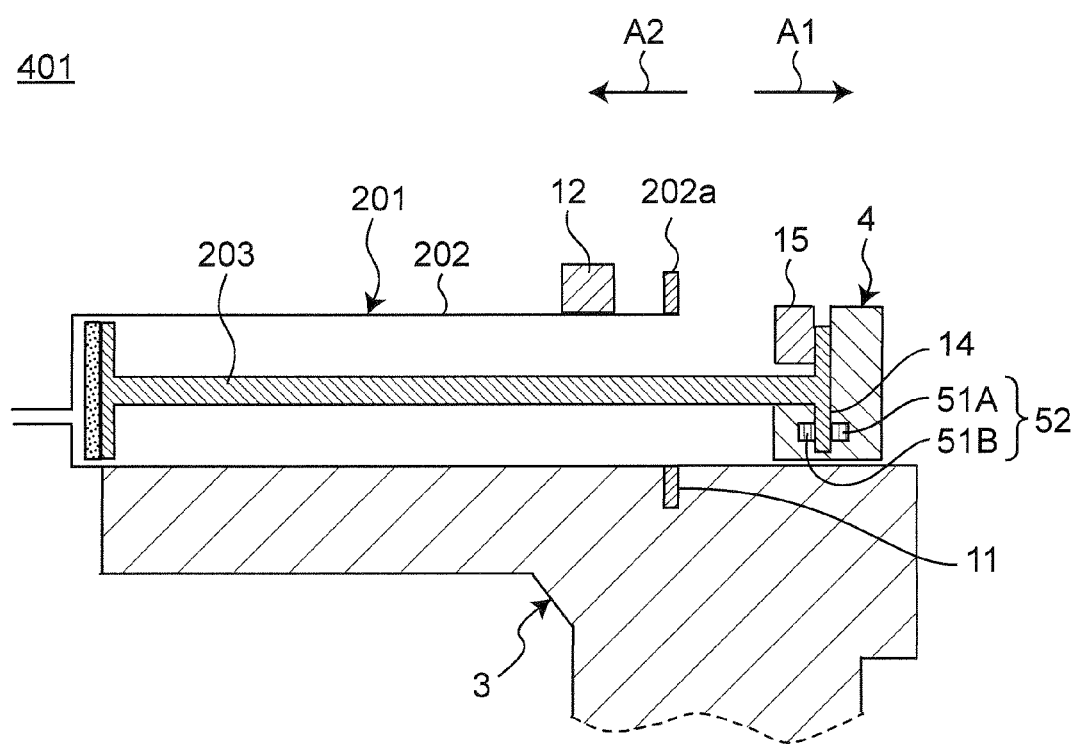
FIG. 9 is a sectional view schematically illustrating a syringe drive device according to an embodiment 2 of the present invention.
Figure 10:
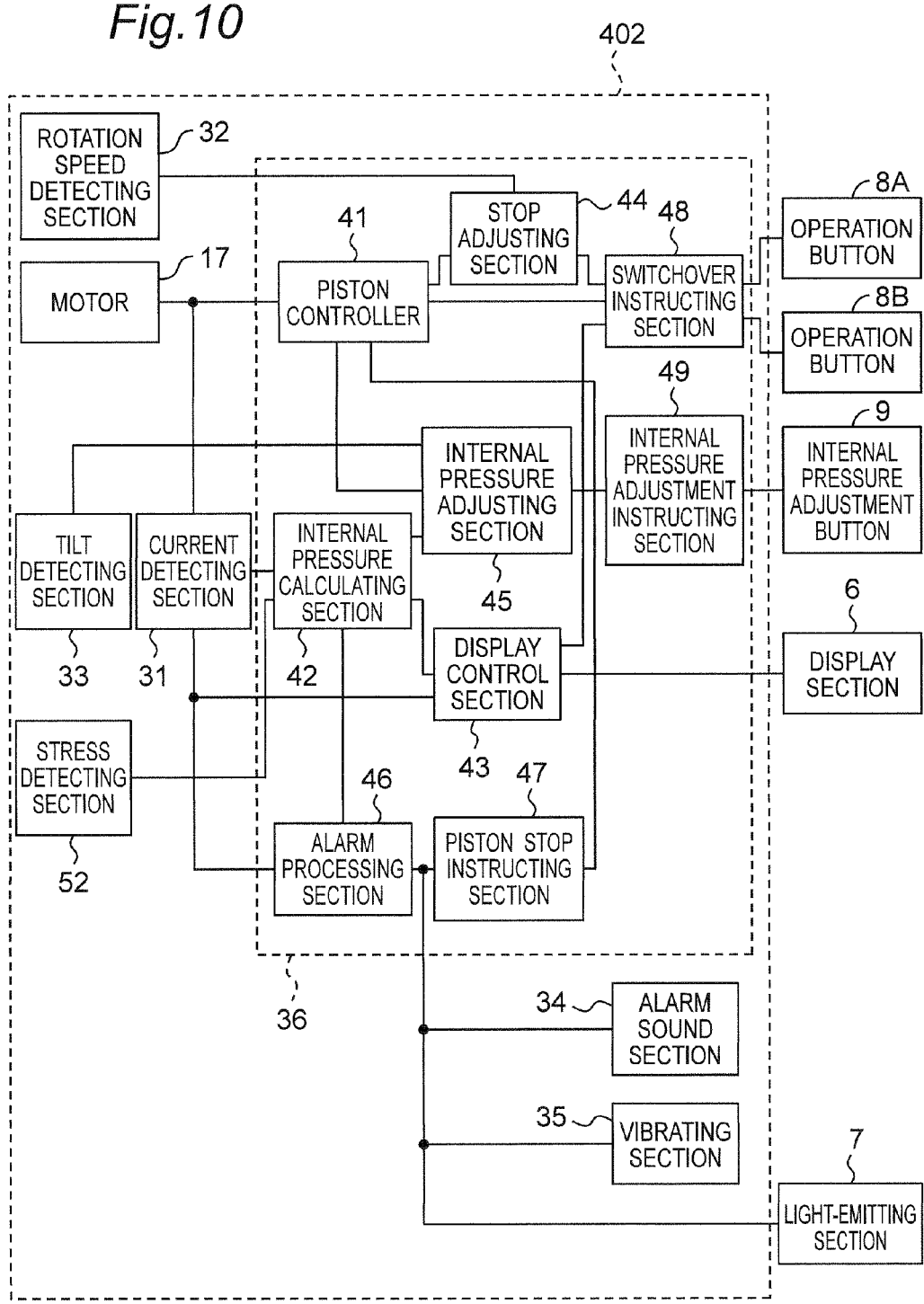
FIG. 10 is a flow chart illustrating processing steps in an operation of the syringe drive device according to the embodiment 2.

In the embodiment 1, the internal pressure of the vial 301 is calculated from the drive current of the motor 17. An embodiment 2 of the present invention illustrated in FIGS. 9 and 10 is different from the embodiment 1 in that the piston manipulating section 4 detects a stress received from the piston 203 and calculates the internal pressure of the vial 301 based on the detected stress. More specifically, a body 402 of a syringe drive device 401 according to the present embodiment is provided with a stress detecting section 52. The stress detecting section 52 has stress sensors 51A and 51B attached to a groove wall of the groove 14 of the piston manipulating section 4. As described earlier, the jaw portion 203a of the piston 203 is fitted in the groove 14 of the piston manipulating section 4, and the coupling piece 15 at the closing position is engaged with the locking claw 16 so that the piston is coupled with the piston manipulating section 4. Then, when a load in the pull-out direction (direction illustrated with arrow A1) is applied to the piston 203, a stress corresponding to the load is detected by the stress sensor 51A. When a load in the push-in direction (direction illustrated with arrow A2) is applied to the piston 203, a stress corresponding to the load is detected by the stress sensor 51B. Therefore, while the injection needle 204 of the syringe 201 is still punctured in the vial 301, the stress corresponding to the internal pressure having a positive value of the vial 301 is detected by the stress sensor 51A, whereas the stress corresponding to the internal pressure having a negative value thereof is detected by the stress sensor 51B.

An operation of the syringe drive device 401 according to the present embodiment is similar to that of the embodiment 1 illustrated in FIGS. 7A and 7B except that the stress is detected by the stress sensor 51A, 51B in Steps S13 and S24, and the internal pressure of the vial 301 is detected in Steps S14 and S25 based on the detected stress (difference between the outputs of the stress sensors 51A and 51B).

Figure 11:
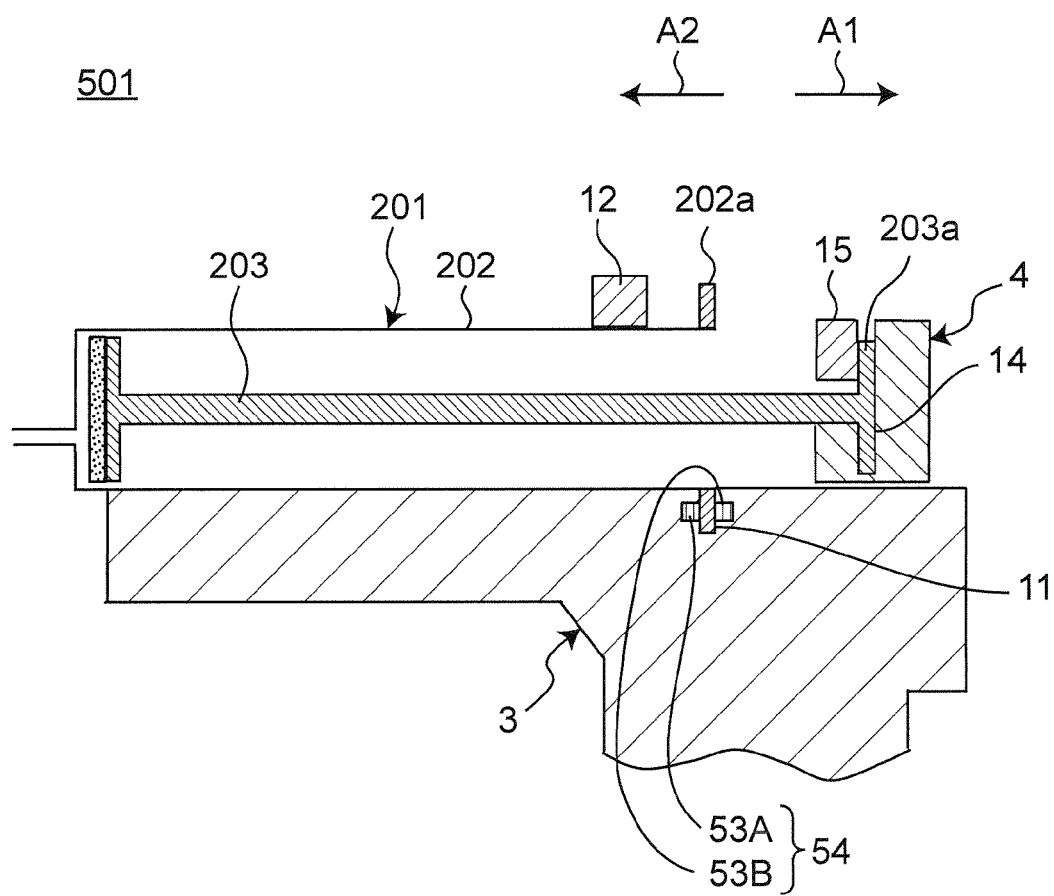
FIG. 11 is a sectional view schematically illustrating a syringe drive device according to a modified embodiment of the embodiment 2.

FIG. 11 illustrates a modified embodiment of the embodiment 2. According to the modified embodiment, a stress detecting section 54 of a syringe drive device 501 has stress sensors 53A and 53B respectively attached to a groove wall of the groove 11 of the syringe holding section 3. As described earlier, the outer tube 202 of the syringe 201 is secured to the syringe holding section 3 in the state where the flange portion 202a is fitted in the groove 11 of the piston holding section 3. Then, when a load in the pull-out direction is applied to the piston 203, a stress corresponding to the load (corresponding to the stress detected by the stress sensor 51A in FIG. 9) is detected by the stress sensor 53A. When a load in the push-in direction is applied to the piston 203, a stress corresponding to the load (corresponding to the stress detected by the stress sensor 51B in FIG. 9) is detected by the stress sensor 53B. Therefore, while the injection needle 204 of the syringe 201 is still punctured in the vial 301, the stress corresponding to the internal pressure having a positive value of the vial 301 is detected by the stress sensor 53A, whereas the stress corresponding to the internal pressure having a negative value of the vial 301 is detected by the stress sensor 53B. The stress thus received by the piston manipulating section 4 from the piston 203 depending on the internal pressure of the vial 301 may be indirectly measured by the flange portion 202a of the outer tube 202.

Embodiment 3

Figure 12:
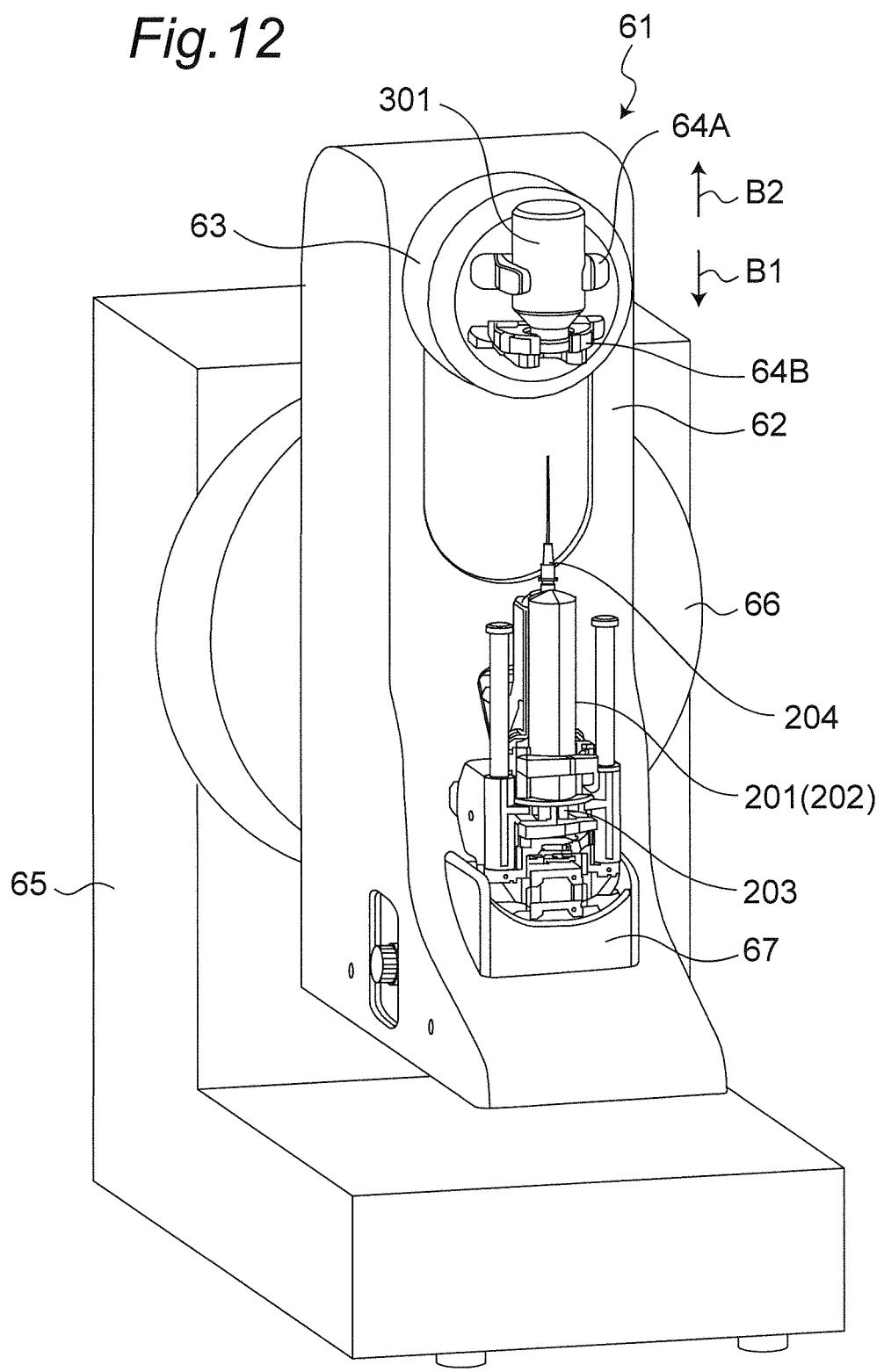
FIG. 12 is a perspective view of a medication dispensing apparatus according to an embodiment 3 of the present invention.

FIG. 12 illustrates a medication dispensing apparatus 61 to which the syringe drive device according to the present invention is applied. The medication dispensing apparatus 61 is configured to aspirate and inject the medicinal solution to and from the syringe 201 and the vial 301. The operator can perform the aspirating and injection by simply manipulating the medication dispensing apparatus 61 without holding the syringe 201 or the vial 301 with hand.

A movable section 62 of the medication dispensing apparatus 61 has a syringe drive device holding section 67 configured to hold a syringe drive device 1 similar to that of the embodiment 1 on one end thereof, and a container holding section 63 on the other end thereof. The container holding section 63 has openable and closable clamps 64A and 64B configured to detachably hold the medicinal solution container (vial 301 in the given example). The container holding section 63 linearly reciprocates to and from the movable section 62 in directions conceptually illustrated with arrows B1 and B2. When the container holding section 63 moves in the direction of arrow B1, the vial 301 moves toward the syringe 201 mounted in the syringe drive device 1. When the container holding section 63 moves in the direction of arrow B2, the vial 301 moves away from the syringe 201. In place of the container holding section 63, the syringe drive device holding section 67 may be configured to move toward and away from the container holding section 63, or the container holding section 63 and the syringe drive device holding section 67 may both linearly reciprocate on the movable section 62.

The movable section 62 is coupled with a stationary pedestal section 65 at a position between the container holding section 63 and the syringe drive device holding section 67. A rotation drive section 66 is interposed between the movable section 62 and the pedestal section 65. As illustrated in FIG. 12, the rotation drive section 66 rotates the movable section 62 to take an upside-down position where the container holding section 63 is positioned on an upper side and the syringe drive device 1 is on a lower side or a regular position opposite to the upside-down position where the syringe drive device 1 is positioned on the lower side and the container holding section 63 is positioned on the upper side.

Figure 13:
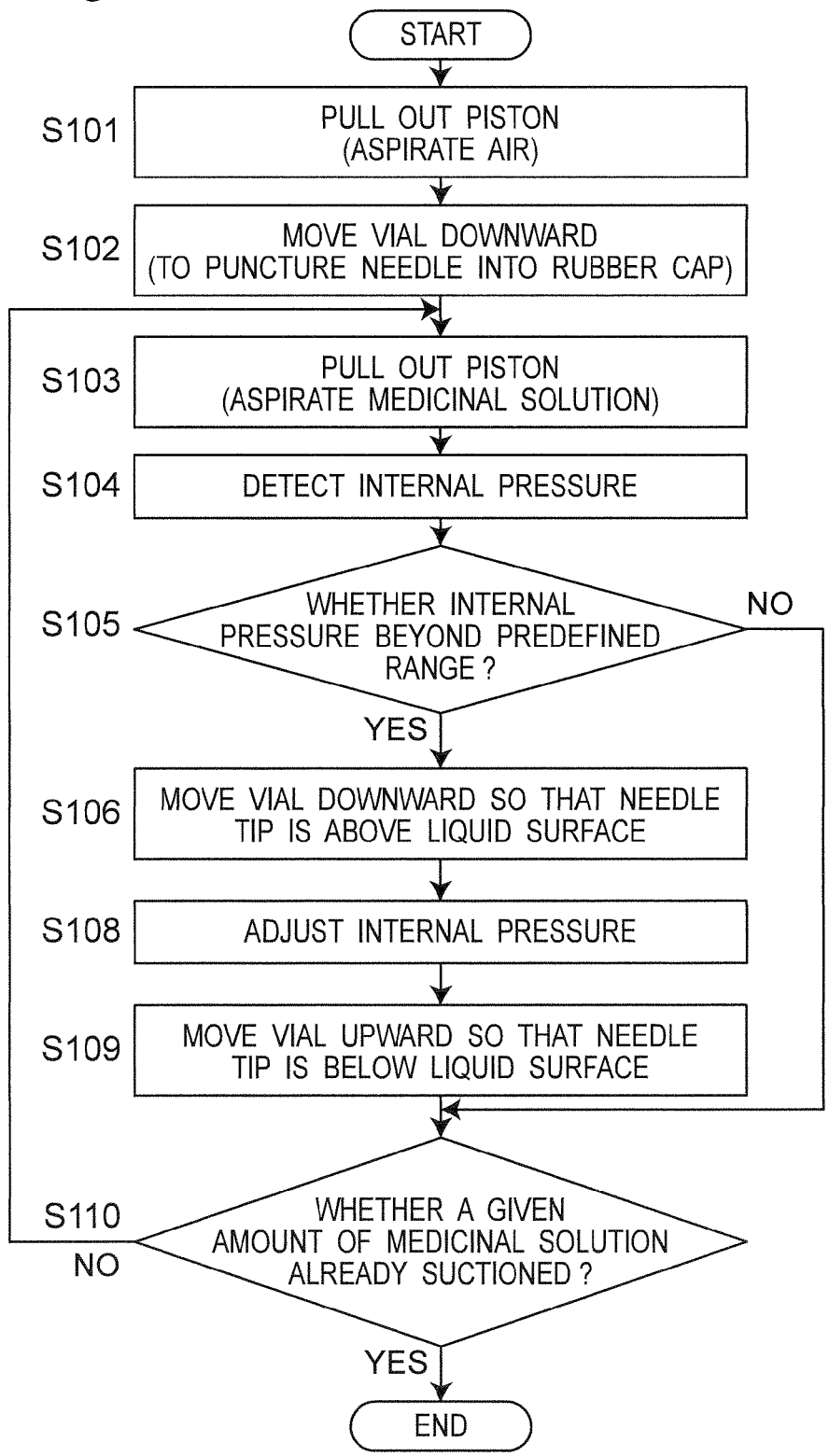
FIG. 13 is a flow chart illustrating an operation for aspirating a medicinal solution from a vial into a syringe in the medication dispensing apparatus according to the embodiment 3.

An operation of the medication dispensing apparatus 61 when the medicinal solution is aspirated from the vial 301 into the syringe 201 is described referring to FIG. 13. An initial position of the movable section 62 is the regular position illustrated in FIG. 12 (syringe drive device holding section 67 is positioned on the lower side, and the container holding section 63 is positioned on the upper side). In Step S101, the piston 203 of the syringe 201 is moved backward by the syringe drive device 1, and air is aspirated into the syringe 201. In Step S103, the vial 301 is moved downward by the container holding section 63 (in the direction of arrow B2), and the injection needle 204 of the syringe 201 is punctured into the vial 301.

In Step S103, the syringe drive device 1 moves the piston 203 in the pull-out direction in Step S103, so that the medicinal solution in the vial 301 is aspirated into the syringe 201. When, in Step S104, it is determined that the internal pressure of the vial 301 detected by the syringe drive device 1 is beyond a given threshold range (Step S105), the container holding section 63 slightly moves the vial 301 downward, so that the tip of the injection needle 204 is above the liquid surface of the medicinal solution in the vial 301. Then, the syringe drive device 1 adjusts the internal pressure (Steps S21 to S29 in FIG. 7B). After that, the vial 301 is moved upward by the container holding section 63, so that the tip of the injection needle 204 is below the liquid surface of the medicinal solution in the vial 301 (Step S109). Operations of steps S103 to S109 are repeatedly carried out until in Step S110, it is determined that a given amount of medicinal solution has been aspirated.

Figure 14:
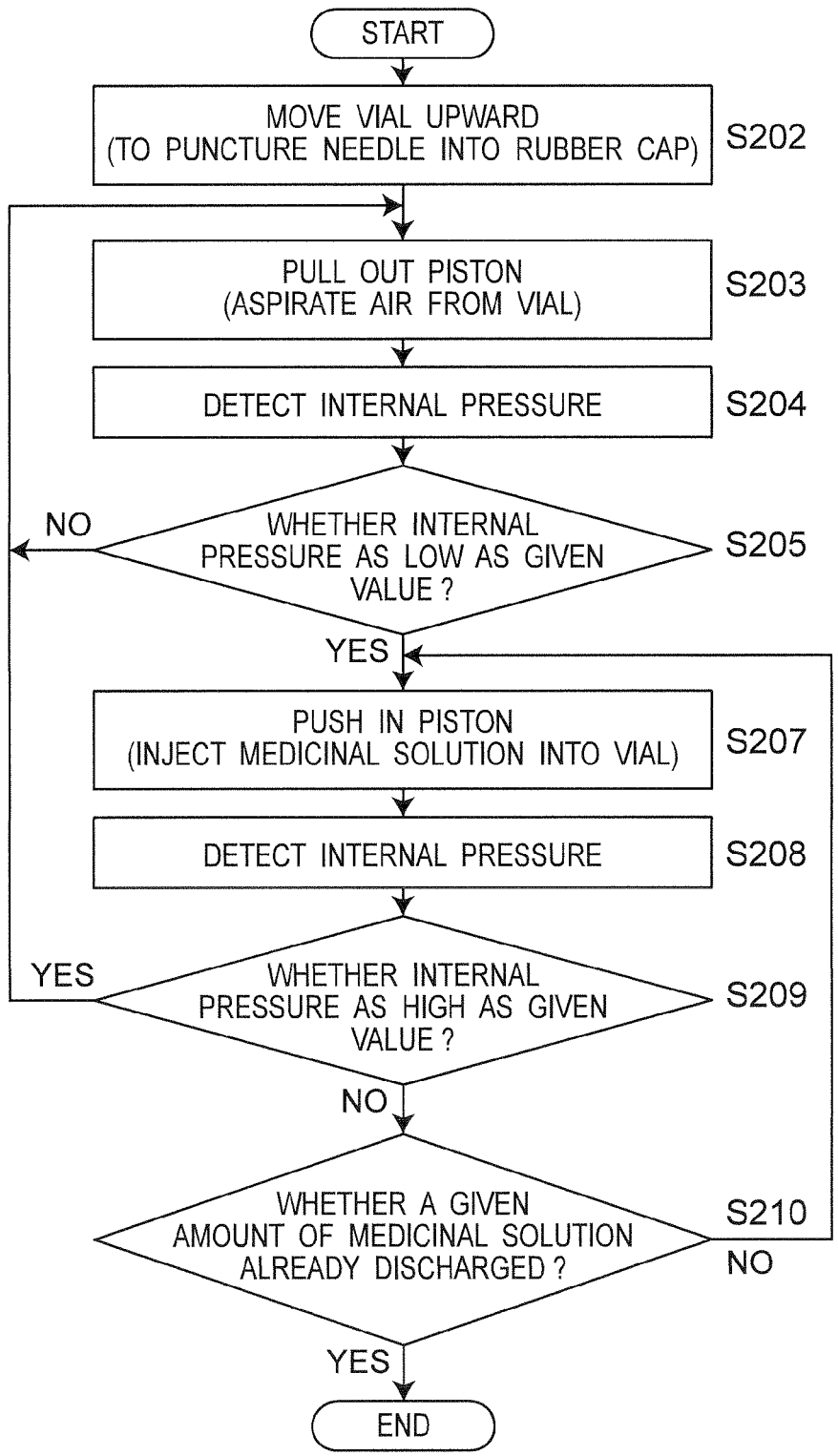
FIG. 14 is a flow chart illustrating an operation for injecting the medicinal solution from the syringe into the vial in the medication dispensing apparatus according to the embodiment 3.
Figure 15:
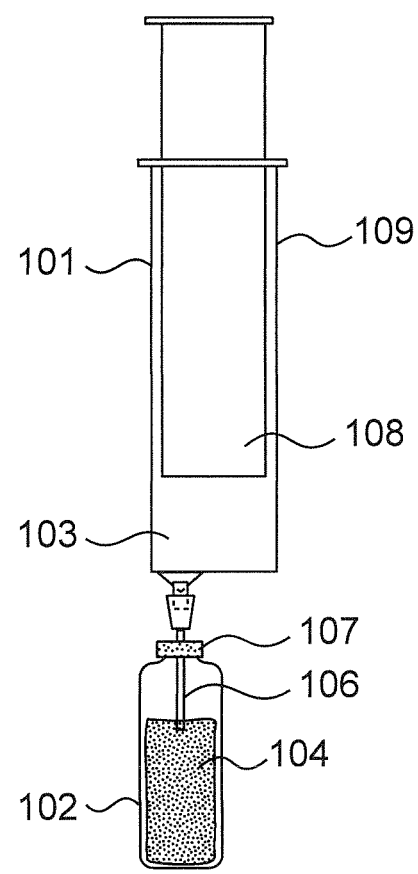
FIG. 15 is an illustration of an operation for aspirating a medicinal solution from a vial using a syringe.

The operation of the medication dispensing apparatus 61 for injecting the medicinal solution from the syringe 201 into the vial 301 is described referring to FIG. 14. The movable position 62 is initially taking the upside-down position opposite to the illustration of FIG. 12. In Step S202, the vial 301 is moved upward by the container holding section 63, so that the injection needle 204 of the syringe 201 is punctured into the vial 301.

In Step S202, the syringe drive device 1 moves the piston 203 in the pull-out direction, so that the air in the vial 301 is aspirated into the syringe 201. In Step S204, the air is continuously aspirated into the syringe 201 until the internal pressure of the vial 301 detected by the syringe drive device 1 is as low as a given value.

When, in Step S204, it is determined that the internal pressure of the vial 301 is as low as the given value, the piston 203 is moved in the push-in direction by the syringe drive device 1, so that the medicinal solution in the syringe 201 is injected into the vial 301. The medicinal solution is repeatedly injected into the vial 301 until, in Step S209, it is determined that the internal pressure of the vial 301 detected by the syringe drive device 1 (Step S208) is as high as a given value or in Step S210, it is determined that a given amount of medicinal solution has been injected. When, in Step S209, it is determined that the internal pressure of the vial 301 increased to reach the given value, Steps S203 to S205 are repeated so that the internal pressure of the vial 301 is reduced.

The present invention can be variously modified as described below.

To be able to accurately estimate and calculate the internal pressure of the vial 301 disregarding any influences of the viscosity resistance, the embodiment 1 calculates the internal pressure of the vial 301 based on the drive current of the motor 17 when the rotation speed of the motor 17 is controlled to be zero. As an alternative method, it is suggested that a friction model be created in advance, in which the following factors are used as parameters; diameters of the syringe 201 and the injection needle 204, shape of a connector between the injection needle 204 and the outer tube 202, viscosity of the medicinal solution 303, coefficient of dynamic friction between the piston 203 and the outer tube 202, and coefficient of dynamic friction and efficiency of a transmission mechanism, and the like. When the measured values of the moving speed of the piston 203 and the drive current of the motor 17 are given to the friction model, the internal pressure of the vial 301 while the piston 203 is being driven can be estimated.

The embodiment 1 provides the light-emitting section 7 to warn the operator apart from the display section 6, however, may, for example, emit a warning light by blinking the display section 6 as a light emitter when an alarm signal is received.

The medicinal solution 303 is not particularly limited as far as it is a fluid material that can be used in the medication dispensing operation such as mixing. For example, the medicinal solution is not necessarily limited to any medicinal solutions in a limited sense such as pharmaceutical products in liquid form, but may be fluid materials for medical use, for example, physiological salt solution. The medicinal solution container is not necessarily limited to the vial 301, but may be other containers including a bag-shape container such as infusion solution bag, ampoule, and bottle as far as the container can have an enclosed space as well as the syringe 201 after the injection needle 204 is punctured therein.

DESCRIPTION OF SYMBOLS

1,401,501 syringe drive device
2 body
2a grip portion
3 syringe holding section
4 piston manipulating section
5 piston drive section
6 display section
7 light-emitting section
8A,8B operation button
9 internal pressure adjustment button
11 groove
12 seizing piece
13,16 locking claw
14 groove
15 coupling piece
17 motor
17a output shaft
18 worm gear
19,22A,22B,23A,23B gear
21 shaft
24A,24B rack
25A,25B bearing
26A,26B fall-out preventing member
27 light-emitting device
28 internal pressure display lamp
29 current display lamp
31 current detecting section
32 rotation speed detecting section
33 tilt detecting section
34 alarm sound section
35 vibrating section
36 controller
41 piston controller
42 internal pressure calculating section
43 display control section
44 stop adjusting section
45 internal pressure adjusting section
46 alarm processing section
47 piston stop instructing section
48 switchover instructing section
49 internal pressure adjustment instructing section
51A,51B stress sensor
52 stress detecting section
61 medication dispensing apparatus
62 movable section
63 container holding section
64A,64B clamp
65 pedestal section
66 rotation drive section
67 syringe drive device holding section
201 syringe
202 outer tube
202a flange portion
203 piston
204 injection needle
301 vial
302 rubber cap
303 medicinal solution

The invention claimed is:

1. A syringe drive device configured to operate a syringe having an outer tube, a piston with an end inserted in the outer tube, and a needle for puncturing a medicinal solution container, the syringe drive device comprising:
- a syringe holding section configured to detachably hold the outer tube of the syringe;
- a piston manipulating section configured to detachably hold the piston of the syringe;
- a piston drive section including a motor, the piston drive section configured to move the piston manipulating section using the motor to thereby move the piston in a direction in which the piston is pushed into the outer tube or a direction in which the piston is pulled out from the outer tube;
- a piston controller configured to change the direction in which the piston manipulating section is moved by the piston drive section using a drive current of the motor;
- an internal pressure measuring section configured to measure an internal pressure of the syringe and the medicinal solution container which is punctured by the needle based on a drive current of the motor; and
- a display section configured to display the internal pressure of the medicinal solution container measured by the internal pressure measuring section.

2. The syringe drive device of claim 1, further comprising:
- a grip portion extending in a direction intersecting with a longitudinal direction of the outer tube of the syringe held by the syringe holding section; and
- an instruction input section used to input an instruction for the piston controller.

3. The syringe drive device of claim 1, wherein the internal pressure measuring section includes:
- a current detecting section configured to detect the drive current of the motor; and
- an internal pressure calculating section configured to calculate the internal pressure of the medicinal solution container based on the drive current detected by the current detecting section.

4. The syringe drive device of claim 3, further comprising:
- a stop adjusting section configured to stop the movement of the piston manipulating section by controlling the drive current,
- wherein the internal pressure calculating section calculates the internal pressure of the medicinal solution container based on the drive current detected by the current detecting section.

5. The syringe drive device of claim 1, further comprising an alarm processing section configured to output an alarm signal when the internal pressure of the medicinal solution container measured by the internal pressure measuring section fails to stay in a predefined numeral range.

6. The syringe drive device of claim 5, further comprising an alarm section configured to output at least one of sound, vibration and light as an alarm call in response to the alarm signal outputted from the alarm processing section.

7. The syringe drive device of claim 5, further comprising a piston stop instructing section configured to stop the movement of the piston manipulating section by controlling the piston drive section in response to the alarm signal outputted from the alarm processing section.

8. The syringe drive device of claim 1, further comprising:
- an internal pressure adjusting section configured to move the piston drive section, when the internal pressure of the medicinal solution container measured by the internal pressure measuring section fails to stay in a predefined numeral range, so that the piston moves to a position where the internal pressure of the medicinal solution container measured by the internal pressure measuring section returns to within the predefined numeral range; and
- an internal pressure adjustment instructing section configured to output an instruction to start to adjust the internal pressure to the internal pressure adjusting section.

9. The syringe drive device of claim 8, wherein the internal pressure adjusting section requests the piston controller to move the piston manipulating section in the direction in which the piston is pulled out from the outer tube when the internal pressure of the medicinal solution container measured by the internal pressure measuring section is equal to or larger than a positive pressure upper-limit value of the predefined numeral range, and
the internal pressure adjusting section requests the piston controller to move the piston manipulating section in the direction in which the piston is pushed into the outer tube when the internal pressure of the medicinal solution container measured by the internal pressure measuring section is equal to or smaller than a negative pressure lower-limit value of the predefined numeral range.

10. The syringe drive device of claim 1, wherein the display section includes a display device which indicates whether the measured internal pressure of the medicinal solution container is included in a predefined numeral range of the internal pressure.

11. The syringe drive device of claim 10, wherein the predefined numeral range of the internal pressure represents an appropriate range of the internal pressure for the needle of the syringe to be pulled out from the medicinal solution container.

12. A medication dispensing device comprising:
- a syringe drive device holding section configured to detachably hold the syringe drive device of claim 1;
- a container holding section configured to detachably hold the medicinal solution container;
- a movable section provided with the syringe drive device holding section on one end thereof and the container holding section on another end thereof, the movable section being configured to move the syringe drive device and the container holding section toward and away from each other;
- a pedestal section configured to rotatably support the movable section between the syringe drive device holding section and the container holding section; and
- a rotation drive section configured to rotate the movable section at a first position at which the syringe drive device holding section is positioned on a lower side and the container holding section is positioned on an upper side, and a second position at which the container holding section is positioned on the upper side and the syringe drive device is positioned on the lower side.

13. A syringe drive device configured to operate a syringe having an outer tube, a piston with an end inserted in the outer tube, and a needle for puncturing a medicinal solution container, the syringe drive device comprising:
- a syringe holding section configured to detachably hold the outer tube of the syringe;
- a piston manipulating section configured to detachably hold the piston of the syringe;
- a piston drive section including a motor, the piston drive section configured to move the piston manipulating section using the motor to thereby move the piston in a direction in which the piston is pushed into the outer tube or a direction in which the piston is pulled out from the outer tube;

a piston controller configured to change the direction in which the piston manipulating section is moved by the piston drive section using a drive current of the motor; and an internal pressure measuring section including a current detecting section configured to detect the drive current of the motor and an internal pressure calculating section configured to calculate the internal pressure of the syringe and the medicinal solution container based on the drive current detected by the current detecting section; and an internal pressure adjusting section configured to move the piston drive section, when the internal pressure of the medicinal solution container measured by the internal pressure measuring section fails to stay in a predefined numeral range, so that the piston moves to a position where the internal pressure of the medicinal solution container measured by the internal pressure measuring section returns to within the predefined numeral range, wherein the predefined numeral range of the internal pressure represents an appropriate range of the internal pressure for the needle of the syringe to be pulled out from the medicinal solution container.

14. The syringe drive device of claim 13, further comprising a display section configured to display the internal pressure of the medicinal solution container measured by the internal pressure measuring section.

* * * * *